US005604099A

United States Patent [19]
Erlich et al.

[11] Patent Number: 5,604,099
[45] Date of Patent: * Feb. 18, 1997

[54] PROCESS FOR DETECTING SPECIFIC NUCLEOTIDE VARIATIONS AND GENETIC POLYMORPHISMS PRESENT IN NUCLEIC ACIDS

[75] Inventors: Henry A. Erlich, Oakland; Glenn Horn, Emeryville; Randall K. Saiki, Richmond; Kary B. Mullis, Kensington, all of Calif.

[73] Assignee: Hoffmann-La Roche Inc., Nutley, N.J.

[ * ] Notice: The term of this patent shall not extend beyond the expiration date of Pat. No. 5,468,613.

[21] Appl. No.: 457,647

[22] Filed: Jun. 1, 1995

Related U.S. Application Data

[63] Continuation of Ser. No. 491,210, Mar. 9, 1990, Pat. No. 5,468,613, which is a continuation-in-part of Ser. No. 839,331, Mar. 13, 1986, abandoned.

[51] Int. Cl.⁶ .............................. C12Q 1/68; C12P 19/34; C12N 9/12; C12N 15/11
[52] U.S. Cl. ..................... 435/6; 435/91.2; 435/91.21; 435/194; 536/24.3; 536/24.33
[58] Field of Search .................... 435/6, 91.1, 91.2, 435/91.21, 194; 536/24.33, 24.3

[56] References Cited

U.S. PATENT DOCUMENTS

| | | | |
|---|---|---|---|
| 3,909,363 | 9/1975 | Bucalo | 435/18 |
| 4,358,535 | 11/1982 | Falkow et al. | 435/5 |
| 4,582,788 | 4/1986 | Erlich | 435/6 |
| 4,605,735 | 8/1986 | Miyoshi et al. | 536/26.3 |
| 4,683,194 | 7/1987 | Saiki et al. | 435/6 |
| 4,683,202 | 7/1987 | Mullis | 435/91.2 |
| 4,685,195 | 7/1987 | Mullis et al. | 435/6 |
| 4,965,189 | 10/1990 | Owerbach | 435/6 |
| 4,971,902 | 11/1990 | Nepom | 435/6 |
| 5,039,606 | 8/1991 | Nepom | 435/6 |
| 5,059,519 | 10/1991 | Owerbach | 435/6 |
| 5,468,613 | 11/1995 | Erlich et al. | 435/6 |

FOREIGN PATENT DOCUMENTS

| | | |
|---|---|---|
| 0111340 | 6/1984 | European Pat. Off. . |
| 0123513 | 10/1984 | European Pat. Off. . |
| 0130515 | 1/1985 | European Pat. Off. . |
| 0164054 | 12/1985 | European Pat. Off. . |
| 0194545 | 9/1986 | European Pat. Off. . |
| 0200362 | 12/1986 | European Pat. Off. . |
| 0228075 | 12/1986 | European Pat. Off. . |
| 0201184 | 12/1986 | European Pat. Off. . |
| 8404332 | 11/1984 | WIPO . |

OTHER PUBLICATIONS

Gilham, Nov. 1964, "The Synthesis of Polynucleotide–Celluloses and Their Use in the Fractionation of Polynucleotides" J. Am Chem. 4982–4985.
Gilham, Nov. 1964, "The Use of Polynucleotide–Celluloses in Sequence Studies of Nucleic Acids" J. Am. Chem. 86:4985–4989.
Wallace et al., 1979, "Hybridization of Synthetic Oligodeoxyribonucleotides to Phi Chi 174 DNA: the Effect of Single Base Pair Mismatch" Nucleic Acids Research 6(11):3543–3557.
Beltz et al., 1983, "Isolation of Multigene Families and Determination of Homologies by Filter Hybridization Methods" Methods Enzymology 100:266–285.
Leary et al., Jul., 1983, "Rapid and Sensitive Colorimetric Method for Visualizing Biotinlabeled DNA Probes Hybridized to DNA or RNA Immobilized on Nitrocellulose: Bio–blots" Proc. Natl. Acad. Sci. USA 80:4045–4049.
Isakov et al., Oct., 1985, "The Tumor Promoter Teleocidin Induces IL–2 Receptor Expression and IL–2 Independent Proliferation of Human Peripheral Blood T Cells" J. Immunology 135(4):2343–2351.
Nagata et al., Apr., 1985, "Quantification of Picogram Levels of Specific DNA Immobilized in Microtiter Wells" FEBS 183(2):379–382.
Salser et al., Genetic Engineering (Chakrabarty, ed.) 1978, pp. 53–81, Entitlted "Cloning cDNA Sequences: A General Technique for Propagating Eukaryotic Gene Sequences in Bacterial Cells".
Kafatos et al., 1979, "Determination of Nucleic Acid Sequence Homologies and Relative Concentrations by a dot Hybridization Procedure" Nucleic Acids Research 7:1541–1552.
Conner et al., 1983, "Detection of Sickle Cell Beta–S–Globin Allele by Hybridization With Synthetic Oligonucleotides" Proc. Natl. Acad. Sci. USA 80:278–282.
Feinberg and Vogelstein, 1983, "A Technique for Radiolabeling DNA Restriction Endonuclease Fragments to High Specific Activity" Analytical Biochemistry 132:6–13.
Gudkov et al., 1983, "Gene Amplification in Mammalian Somatic Cells Resistant to Colchicine. Part VI Analysis of Amplified DNA Sequences by Restriction Endonuclease Digestion" Chem. Abstract 99:156 (no. 153092a).
Kidd et al., 1983, "Alpha 1–Antitrypsin Deficiency Detection by Direct Analysis of the Mutaiton in the Gene" Nature 304:230–234.
Owerbach et al., 1983, "HLA–D Region Beta–Chain DNA Endonuclease Fragments Differ Between HLA–DR Identical Healthy and Insulin–Dependent Diabetic Individuals" Nature 303:815–817.

(List continued on next page.)

*Primary Examiner*—James S. Ketter
*Attorney, Agent, or Firm*—George W. Johnston; Stacey R. Sias; Douglas A. Petry

[57] ABSTRACT

Single or multiple nucleotide variations in nucleic acid sequence can be detected in nucleic acids by a process whereby the sample suspected of containing the relevant nucleic acid is repeatedly treated with primers, nucleotide triphosphates, and an agent for polymerization of the triphosphates and then denatured, in a process which amplifies the sequence containing the nucleotide variation if it is present. In one embodiment, the sample is spotted on a membrane and treated with a labeled sequence-specific oligonucleotide probe. Hybridization of the probe to the sample is detected by the label on the probe.

32 Claims, No Drawings

OTHER PUBLICATIONS

Pirastu et al., 1983, "Prenatal Diagnosis of Beta–Thalassemia—Detection of a Single Nucleotide Mutation in DN" N. Eng. J. Med. 309:284–287.

Meinkoth and Wahl, 1984, "Hybridization of Nucleic Acids Immobilized on Solid Supports" Analytical Biochemistry 138:267–284.

Bell et al., May, 1985, "DNA Sequence and Characterization of Human Class II Major Histocompatibility Complex B–Chains From the DR1 Haplotype" Proc. Natl. Acad. Sci. USA 82:3405–3409.

Gaubatz et al., 1985, "Displacement Synthesis of Globin Complementary DNA: Evidence for Sequence Amplification" Chem. Abst. 103:186(No. 117310n).

Gaubatz and Paddock, 1985, "Displacement Synthesis of Globin Complementary DNA: Evidence for Sequence Amplification" Biochimica et Biophysica Acta 825:175–187.

Langdale and Malcolm, 1985, "A Rapid Method of Gene Detection Using DNA Bound to Sephacryl" Gene 36:201–210.

Myers et al., 1985, "Detection of Single Base Substitutions by Ribonuclease Cleavage at Mismatches in RNA: DNA Duplexes" Science 230: 1242–1246.

Reed and Mann, 1985, "Rapid Transfer of DNA From Agarose Gels to Nyon Membranes" Nucleic Acids Research 13(20):7207–7221.

Saiki et al., 1985, "Enzymatic Amplification of Beta–Globoin Genomic Sequences and Restriction Site Analysis for Diagnosis of Sickle Cell Anemia" Science 230:1350–1354.

Saiki et al., Nov., 1985, "A Novel Method for the Detection of Polymorphic Restriction Sites by Cleavage of Oligonucleotide Probes: Application to Sickle–Cell Anemia" Bio/Technology 3(11):1008–1012.

Winter et al., 1985, "A Method to Detection and Characterize Point Mutations in Transcribed Genes: Amplification and Overexpression of the Mutant c–Ki–ras Allele in Human Tumor Cells" Proc. Natl. Acad. Sci. USA 82:7575–7579.

Cummings et al., 1986, "Excision–Amplification of Mitochondrial DNA During Senescence in Podospora Anserina. DNA Sequence Analysis of Three Unique 'Plasmids'" Chem. Abst. 104:163 (No. 62996d).

Cummings et al., 1986, "Excision–Amplification of Mitochondrial DNA During Senescence in Podospora Anserina. DNA Sequence Analysis of Three Unique 'Plasmids'" J. Mol. Biol. 185:659–680.

Kalisch et al., 1986, "Covalently Linked Sequencing Primer Linkers (Spliners) for Sequence Anaylsis of Restriction Fragments" Gene 44:263–270.

Mullis et al., 1986, "Specific Enzymatic Amplification of DNA In Vitro: The Polymerase Chain Reaction" CSH Symp. Quant. Biol. 51:263–273.

Sanger et al., Feb., 1977, "Nucleotide Sequence of Bacteriophage PhiX174 DNA" Nature 265:687–695.

Erlich et al., Dec., 1984, "Analysis by Molecular Cloning of the Human Class II Genes" Federation Proceedings 43(15):3025–3030.

5,604,099

PROCESS FOR DETECTING SPECIFIC NUCLEOTIDE VARIATIONS AND GENETIC POLYMORPHISMS PRESENT IN NUCLEIC ACIDS

This application is a continuation of U.S. application Ser. No. 07/491,210, filed Mar. 9, 1990, now U.S. Pat. No. 5,468,613 which is a continuation-in-part application of now abandoned U.S. Ser. No. 839,331, filed Mar. 13, 1986, and is related to U.S. Pat. No. 4,683,195, filed Feb. 7, 1986, which is a continuation-in-part of U.S. Pat. No. 4,683,202, filed Oct. 25, 1985, which is a continuation-in-part of U.S. Ser. No. 716,975, filed Mar. 28, 1985, now abandoned. This application is also related to U.S. Ser. No. 899,061, filed Aug. 22, 1986, which is a CIP of U.S. Ser. No. 833,368 filed Feb. 25, 1986, now abandoned U.S. Ser. No. 899,241, filed Aug. 22, 1986, and copending U.S. Ser. No. 899,512, filed Aug. 22, 1986.

BACKGROUND OF THE INVENTION

This invention relates to a process for detecting nucleotide variations, mutations and polymorphisms by amplifying nucleic acid sequences suspected of containing such mutations or polymorphisms and detecting them with sequence-specific oligonucleotides in a dot blot format.

In recent years, the molecular basis of a number of human genetic diseases has been elucidated by the application of recombinant DNA technology. In particular, the detection of specific polymorphic restriction sites in human genomic DNA associated with genetic disease, such as sickle-cell anemia, has provided clinically valuable information for prenatal diagnosis. In these studies, the presence or absence of a specific site is revealed by restriction fragment length polymorphism (RFLP) analysis, a method in which variation in the size of a specific genomic restriction fragment is detected by Southern blotting and hybridization of the immobilized genomic DNA with a labeled probe. RFLP analysis has proved useful in the direct detection of polymorphic sites that contain the mutation conferring the disease phenotype (e.g., MstII and sickle-cell anemia) as well as in linkage studies where a particular allelic restriction site is linked to a disease locus within a family but not necessarily in the general population. See, for example, Kan and Dozy, *Proc. Natl. Acad. Sci. USA*, 75, 5631 (1978), and Rubin and Kan, *Lancet*, 1985-I, 75 (1985). See also Geever et al., *Proc. Natl. Acad. Sci. USA*, 78, 5081 (1981) and Wilson et al., *Proc. Natl. Acad. Sci. USA*, 79, 3628 (1982).

In a second method, called "oligomer restriction", a synthetic end-labeled oligonucleotide probe is annealed in solution to the target genomic DNA sequence and a restriction enzyme is added to cleave any hybrids formed. This method, the specificity of which depends on the ability of a base pair mismatch within the restriction site to abolish or inhibit cleavage, is described more fully by Saiki et al., *Biotechnology*, 3, 1008–1012 (1985). In addition, the sensitivity of this technique may be enhanced by utilizing a polymerase chain reaction procedure wherein the sample is first subjected to treatment with specific primers, polymerase and nucleotides to amplify the signal for subsequent detection. This is described more fully by Saiki et al., *Science*, 230, 1350–1353 (1985) and in U.S. Pat. No. 4,683,202.

A third method for detecting allelic variations which is independent of restriction site polymorphism utilizes sequence-specific synthetic oligonucleotide probes. See Conner et al., *Proc. Natal. Acad. Sci. USA*, 80, 78 (1983). This latter technique has been applied to the prenatal diagnosis of αl-antitrypsin deficiency (Kidd et al., *Nature*, 304, 230 (1983)) and β-thalassemia (Pirastu et al., *N. Eng. J. Med.*, 309, 284 (1983)). In addition, the technique has been applied to study the polymorphism of HLA-DRβ using Southern blotting (Angelini et al., *Proc. Natl. Acad. Sci. USA*, 83, 4489–4493 (1986)).

The basis for this procedure is that under appropriate hybridization conditions a short oligonucleotide probe of at least 19 bases (19-mer) will anneal only to those sequences to which it is perfectly matched, a single base pair mismatch being sufficiently destabilizing to prevent hybridization. The distinction between the allelic variants is based on the thermal stability of the duplex formed between the genomic DNA and the oligonucleotide (19-mer) probe.

In addition, methods for detecting base pair mismatches in double-stranded RNA and RNA:DNA heteroduplexes have been described using pancreatic ribonuclease (RNase A) to cleave the heteroduplexes. Winter et al., *Proc. Natl. Acad. Sci. USA*, 82:7575–7579 (1985) and Myers et al., *Science*, 23(230:1242–1246 (1985). The principal deficiency of this method is its inability to recognize all types of base pair mismatches.

Both the RFLP and oligonucleotide probe stability methods are relatively complex procedures, requiring restriction enzyme digestion, gel-fractionation of the genomic DNA, denaturation of the DNA, immobilization of the DNA either by transfer to a filter membrane or dessication of the gel itself, and hybridization of a labeled probe to the electrophoretically resolved array of immobilized genomic restriction fragments. These steps are necessary, for the oligonucleotide probe stability method, due to the complexity of human genomic DNA. Restriction and electrophoresis are necessary to separate the target sequence ("signal") from the rest of the genome ("noise"), and hybridization in the gel (instead of filter transfer) is necessary to retain as much target sequence as possible. Even then, detection of a signal in a 10 μg sample using a high specific activity kinased probe requires an autoradiographic exposure of four days.

In addition, the approach of Conner et al. requires at least a 19-mer probe for reasons of specificity (a shorter probe would hybridize to more genomic fragments), as well as possibly sensitivity. Shorter probes (e.g., 16-mers), however, would show more sequence-specific discrimination because a single mismatch would be more destabilizing.

There is a need in the art for a simplified method with improved sensitivity and specificity for directly detecting single-base differences in nucleic acids such as genomic DNA.

SUMMARY OF THE INVENTION

Accordingly, the present invention provides a method for detecting single or multiple nucleotide variations in nucleic acid sequence from any source, for use in detecting any type of disease or condition. The method herein directly detects the sequence variation, eliminating the need for restriction digestion, electrophoresis, and gel manipulations otherwise required. In addition, the method herein provides for improved specificity and sensitivity of the probe; an interpretable signal can be obtained with a 0.04 μg sample in six hours. Thirdly, if the amount of sample spotted on a membrane is increased to 0.1–0.5 μg, non-isotopically labeled oligonucleotides may be utilized rather than the radioactive probes used in previous methods. Finally, the process herein is applicable to use of sequence-specific oligonucleotides less than 19-mers in size, thus allowing use of more discriminatory sequence-specific oligonucleotides.

Specifically, the present invention provides for a process for detecting the presence or absence of at least one nucleotide variation in sequence in one or more double-stranded nucleic acids contained in a sample, which process comprises:

(a) treating the sample, together or sequentially, with four different nucleoside triphosphates, an agent for polymerization of the nucleoside triphosphates, and one oligonucleotide primer for each strand of each nucleic acid suspected of containing said variation under hybridizing conditions, such that for each nucleic acid strand containing each different variation to be detected, an extension product of each primer is synthesized which is complementary to each nucleic acid strand, wherein said primer or primers are selected so as to be substantially complementary to each nucleic acid strand containing each different variation, such that the extension product synthesized from one primer, when it is separated from its complement, can serve as a template for synthesis of the extension product of the other primer;

(b) treating the sample under denaturing conditions to separate the primer extension products from their templates if the variation(s) to be detected are present;

(c) treating the sample, together or sequentially, with said four nucleoside triphosphates, an agent for polymerization of the nucleoside triphosphates, and oligonucleotide primers such that a primer extension product is synthesized using each of the single strands produced in step (b) as a template, wherein steps (b) and (c) are repeated a sufficient number of times to result in detectable amplification of the nucleic acid containing the sequence variation(s), if present;

(d) affixing the product of step (c) to a membrane;

(e) treating the membrane under hybridization conditions with a labeled sequence-specific oligonucleotide probe capable of hybridizing with the amplified nucleic acid sequence only if a sequence of the probe is complementary to a region of the amplified sequence; and (f) detecting whether the probe has hybridized to an amplified sequence in the nucleic acid sample.

Steps (b) and (c) are preferably repeated at least five times, and more preferably 15–30 times if the sample contains human genomic DNA. If the sample comprises cells, preferably they are heated before step (a) to expose the nucleic acids therein to the reagents. This step avoids purification of the nucleic acids prior to reagent addition.

In a variation of this process, the primer(s) and/or nucleoside triphosphates are labeled so that the resulting amplified sequence is labeled. The labeled primer(s) and/or nucleoside triphosphate(s) can be present in the reaction mixture initially or added during a later cycle. The sequence-specific oligonucleotide (unlabeled) is affixed to a membrane and treated under hybridization conditions with the labeled amplification product so that hybridization will occur only if the membrane-bound sequence is present in the amplification product.

In another embodiment, the invention herein relates to a kit for detecting the presence or absence of at least one nucleotide variation in sequence in one or more nucleic acids contained in a sample, which kit comprises, in packaged form, a multicontainer unit having:

(a) one container for each oligonucleotide primer for each nucleic acid strand containing each different variation being detected, which primer(s) are substantially complementary to each strand containing each different variation, such that an extension product synthesized from one primer, when it is separated from its complement, can serve as a template for the synthesis of the extension product of the other primer so as to produce one or more amplified nucleic acid sequences if the sequence variation(s) are present;

(b) a container for an agent for polymerization;

(c) a container for each of four different nucleoside triphosphates;

(d) one container for each labeled sequence-specific oligonucleotide capable of hybridizing with each possible sequence variation in the amplified nucleic acid sequence; and (e) container(s) for reagents which detect hybridization of the probes to the amplified sequence.

Regarding genetic diseases, while RFLP requires a polymorphic restriction site to be associated with the disease, sequence-specific oligonucleotides directly detect the genetic lesion and are generally more useful for the analysis of such genetic diseases as hemoglobin C disease, αl-antitrypsin and β-thalassemia which result from single or multiple base mutations. In addition, the oligonucleotides can be used to distinguish between genetic variants which represent different alleles (e.g., HLA typing), indicating the feasibility of a sequence-specific oligonucleotide-based HLA typing kit.

DESCRIPTION OF THE PREFERRED EMBODIMENTS

The term "nucleotide variation in sequence" refers to any single or multiple nucleotide substitutions, deletions or insertions. These nucleotide variations may be mutant or polymorphic allele variations. Therefore, the process herein can detect single nucleotide changes in nucleic acids such as occur in β-globin genetic diseases caused by single-base mutations, additions and deletions (some β-thalassemias, sickle cell anemia, hemoglobin C disease, etc.), as well as multiple-base variations such as are involved with α-thalassemia or some β-thalassemias. The process can al so detect polymorphisms, which are not necessarily associated with a disease, but are merely a condition in which two or more different nucleotide sequences (whether having substituted, deleted or inserted nucleotide base pairs) can exist at a particular site in the nucleic acid in the population, as with HLA regions of the human genome and random polymorphisms such as in mitochondrial DNA. The polymorphic sequence-specific oligonucleotide probes described in detail hereinafter may be used as genetic markers linked to a disease such as insulin-dependent diabetes or in forensic applications. If the nucleic acid is double-stranded, the nucleotide variation in sequence becomes a base pair variation in sequence.

The term "oligonucleotide" as used herein is defined as a molecule comprised of two or more deoxyribonucleotides or ribonucleotides, preferably more than three. Its exact size will depend on many factors, which in turn depend on the ultimate function or use of the oligonucleotide. The oligonucleotide may be derived synthetically or by cloning.

The term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of four different nucleoside triphosphates and an agent for polymerization such as DNA polymerase in an appropriate buffer ("buffer" includes pH, ionic strength, cofactors, etc.) and at a suitable temperature.

The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primer and use of the method. For example, depending on the complexity of the target sequence, the oligonucleotide primer typically contains 15–25 nucleotides, although it may contain more or fewer nucleotides. Short primer molecules generally require lower temperatures to form sufficiently stable hybrid complexes with the template.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Typically, the primers have exact complementarity to obtain the best detection results.

The term "sequence-specific oligonucleotides" refers to oligonucleotides which will hybridize to specific sequences, whether or not contained on alleles which sequences span the nucleotide variation being detected and are specific for the sequence variation being detected. Depending on the sequences being analyzed, one or more sequence-specific oligonucleotides may be employed for each sequence, as described further below.

As used herein, the term "thermostable enzyme" refers to an enzyme which is stable to heat and is heat resistant and catalyzes (facilitates) combination of the nucleotides in the proper manner to form the primer extension products which are complementary to each nucleic acid strand. Generally, the synthesis will be initiated at the 3' end of each primer and will proceed in the 5' direction along the template strand, until synthesis terminates, producing molecules of different lengths. There may be thermostable enzymes, however, which initiate synthesis at the 5' end and proceed in the other direction, using the same process as described above. A purified thermostable enzyme and method for using it are described more fully in now abandoned U.S. Ser. Nos. 899,241 and 899,513, both filed Aug. 22, 1986, the disclosures of which are incorporated herein by reference.

The present invention is directed to a process for amplifying any one or more specific nucleic acid sequences (as defined herein to contain one or more nucleotide variations) suspected of being in one or more nucleic acids.

In general, the present process involves a chain reaction for producing, in exponential quantities relative to the number of reaction steps involved, at least one specific nucleic acid sequence given (a) that the ends of the required sequence are known in sufficient detail that oligonucleotides can be synthesized which will hybridize to them, and (b) that a small amount of the sequence is available to initiate the chain reaction. The product of the chain reaction will be a discrete nucleic acid duplex with termini corresponding to the ends of the specific primers employed.

Any nucleic acid, in purified or nonpurified form, can be utilized as the starting nucleic acid or acids, provided it is suspected of containing the sequence being detected. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid.

It is not necessary that the sequence to be amplified be present initially in a pure form; it may be a minor fraction of a complex mixture, such as a portion of the β-globin gene contained in whole human DNA, or a portion of nucleic acid sequence due to a particular microorganism which organism might constitute only a very minor fraction of a particular biological sample. The starting nucleic acid may contain more than one desired specific nucleic acid sequence which may be the same or different. Therefore, the present process is useful not only for producing large amounts of one specific nucleic acid sequence, but also for amplifying simultaneously more than one different specific nucleic acid sequence located on the same or different nucleic acid molecules if more than one of the base pair variations in sequence is present.

The nucleic acid or acids may be obtained from any source, for example, from plasmids such as pBR322, from cloned DNA or RNA, or from natural DNA or RNA from any source, including bacteria, yeast, viruses, organelles, and higher organisms such as plants or animals. DNA or RNA may be extracted from blood, tissue material such as chorionic villi or amniotic cells by a variety of techniques such as that described by Maniatis et al., *Molecular Cloning* (1982), 280–281.

The cells may be directly used without purification of the nucleic acid if they are suspended in hypotonic buffer and heated to about 90°–100° C., until cell lysis and dispersion of intracellular components occur, generally about 1 to 15 minutes. After the heating step the amplification reagents may be added directly to the lysed cells. This direct cell detection method may be used on peripheral blood lymphocytes and amniocytes.

Any specific nucleic acid sequence can be amplified by the present process. It is only necessary that a sufficient number of bases at both ends of the sequence be known in sufficient detail so that two oligonucleotide primers can be prepared which will hybridize to different strands of the desired sequence and at relative positions along the sequence such that an extension product synthesized from one primer, when it is separated from its template (complement), can serve as a template for extension of the other primer into a nucleic acid of defined length. The greater the knowledge about the bases at both ends of the sequence, the greater can be the specificity of the primers for the target nucleic acid sequence, and thus the greater the efficiency of the process.

It will be understood that the word "primer" as used hereinafter may refer to more than one primer, particularly in the case where there is some ambiguity in the information regarding the terminal sequence(s) of the fragment to be amplified. For instance, in the case where a nucleic acid sequence is inferred from protein sequence information, a collection of primers containing sequences representing all possible codon variations based on degeneracy of the genetic code will be used for each strand. One primer from this collection will be homologous with the end of the desired sequence to be amplified.

The oligonucleotide primers may be prepared using any suitable method, such as, for example, the organic synthesis of a nucleic acid from nucleoside derivatives. This synthesis may be performed in solution or on a solid support. One type of organic synthesis is the phosphotriester method, which has been utilized to prepare gene fragments or short genes. In the phosphotriester method, oligonucleotides are prepared that can then be joined together to form longer nucleic acids. For a description of this method, see Narang, S. A., et al., *Meth. Enzymol.*, 68, 90 (1979) and U.S. Pat. No. 4,356,270. The patent describes the synthesis and cloning of the somatostatin gene.

A second type of organic synthesis is the phosphodiester method, which has been utilized to prepare a tRNA gene. See Brown, E. L., et al., *Meth. Enzymol.*, 68, 109 (1979) for a description of this method. As in the phosphotriester method, this phosphodiester method involves synthesis of oligonucleotides that are subsequently joined together to form the desired nucleic acid.

Automated embodiments of these methods may also be employed. In one such automated embodiment, diethylphosphoramidites are used as starting materials and may be synthesized as described by Beaucage et al., *Tetrahedron Letters* (1981), 22:1859–1862. One method for synthesizing oligonucleotides on a modified solid support is described in U.S. Pat. No. 4,458,066. It is also possible to use a primer which has been isolated from a biological source (such as a restriction endonuclease digest).

The specific nucleic acid sequence is produced by using the nucleic acid containing that sequence as a template. If the nucleic acid contains two strands, it is necessary to separate the strands of the nucleic acid before it can be used as the template, either as a separate step or simultaneously with the synthesis of the primer extension products. This strand separation can be accomplished by any suitable denaturing method including physical, chemical or enzymatic means. One physical method of separating the strands of the nucleic acid involves heating the nucleic acid until it is completely (>99%) denatured. Typical heat denaturation may involve temperatures ranging from about 80° to 105° C. for times ranging from about 1 to 10 minutes. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Kuhn Hoffmann-Berling, *CSH-Quantitative Biology*, 43:63 (1978), and techniques for using RecA are reviewed in C. Radding, *Ann. Rev. Genetics.*, 16:405–37 (1982).

If the original nucleic acid containing the sequence variation to be amplified is single stranded, its complement is synthesized by adding one or two oligonucleotide primers thereto. If an appropriate single primer is added, a primer extension product is synthesized in the presence of the primer, an agent for polymerization, and the four nucleoside triphosphates, as described below. The product will be partially complementary to the single-stranded nucleic acid and will hybridize with the nucleic acid strand to form a duplex of unequal length strands that may then be separated into single strands as described above to produce two single separated complementary strands. Alternatively, two appropriate primers may be added to the single-stranded nucleic acid and the reaction carried out.

If the original nucleic acid constitutes the entire sequence variation to be amplified, the primer extension product(s) produced will be completely complementary to the strands of the original nucleic acid and will hybridize therewith to form a duplex of equal length strands to be separated into single-stranded molecules.

When the complementary strands of the nucleic acid or acids are separated, whether the nucleic acid was originally double or single stranded, the strands are ready to be used as a template for the synthesis of additional nucleic acid strands. This synthesis can be performed using any suitable method. Generally it occurs in a buffered aqueous solution, preferably at a pH of 7–9, most preferably about 8. Preferably, a molar excess (for cloned nucleic acid, usually about 1000:1 primer:template, and for genomic nucleic acid, usually about $10^6$:1 primer:template) of the two oligonucleotide primers is added to the buffer containing the separated template strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP and TTP are also added to the synthesis mixture in adequate amounts and the resulting solution is heated to about 90°–100° C. for from about 1 to 10 minutes, preferably from 1 to 4 minutes. After this heating period the solution is allowed to cool to room temperature, which is preferable for the primer hybridization. To the cooled mixture is added an agent for polymerization, and the reaction is allowed to occur under conditions known in the art. This synthesis reaction may occur at from room temperature up to a temperature above which the inducing agent no longer functions efficiently. Thus, for example, if an *E. coli* DNA polymerase is used as agent for polymerization, the temperature is generally no greater than about 40° C. Most conveniently the reaction occurs at room temperature.

The agent for polymerization of the nucleoside triphosphates may be any compound or system which will function to accomplish the synthesis of primer extension products, including enzymes. Suitable enzymes for this purpose include, for example, *E. coli* DNA Polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be agents, however, which initiate synthesis at the 5' end and proceed in the other direction, using the same process as described above.

The newly synthesized strand and its complementary nucleic acid strand form a double-stranded molecule which is used in the succeeding steps of the process. In the next step, the strands of the double-stranded molecule are separated using any of the procedures described above to provide single-stranded molecules.

New nucleic acid is synthesized on the single-stranded molecules. Additional agent for polymerization, nucleotides and primers may be added if necessary for the reaction to proceed under the conditions prescribed above. Again, the synthesis will be initiated at one end of the oligonucleotide primers and will proceed along the single strands of the template to produce additional nucleic acid. After this step, half of the extension product will consist of the specific nucleic acid sequence bounded by the two primers.

The steps of strand separation and extension product synthesis can be repeated as often as needed to produce the desired quantity of the specific nucleic acid sequence. As will be described in further detail below, the amount of the specific nucleic acid sequence produced will accumulate in an exponential fashion.

When it is desired to produce more than one specific nucleic acid sequence from the first nucleic acid or mixture of nucleic acids, the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process.

The present invention can be performed in a step-wise fashion where after each step new reagents are added, or simultaneously, where all reagents are added at the initial step, or partially step-wise and partially simultaneous, where fresh reagent is added after a given number of steps. If a method of strand separation, such as heat, is employed which will inactivate the inducing agent, as in the case of a heat-labile enzyme, then it is necessary to replenish the agent for polymerization after every strand separation step. The simultaneous method may be utilized when an enzymatic means is used for the strand separation step. In the simultaneous procedure, the reaction mixture may contain, in addition to the nucleic acid strand(s) containing the desired sequence, the strand-separating enzyme (e.g., helicase), an appropriate energy source for the strand-separating enzyme, such as rATP, the four nucleotides, the oligonucleotide primers in molar excess, and the inducing agent, e.g., Klenow fragment of *E. coli* DNA Polymerase I.

If heat is used for denaturation in a simultaneous process, a heat-stable enzyme such as a thermostable polymerase may be employed which will operate at an elevated temperature, preferably 65°–90° C. depending on the agent for polymerization, at which temperature the nucleic acid will consist of single and double strands in equilibrium. For smaller lengths of nucleic acid, lower temperatures of about 50° C. may be employed. The upper temperature will depend on the temperature at which the enzyme will degrade or the temperature above which an insufficient level of primer hybridization will occur. Such a heat-stable enzyme is described, e.g., by A. S. Kaledin et al., *Biokhimiya*, 45, 644–651 (1980). Each step of the process will occur sequentially notwithstanding the initial presence of all the reagents. Additional materials may be added as necessary. After the appropriate length of time has passed to produce the desired amount of the specific nucleic acid sequence, the reaction may be halted by inactivating the enzymes in any known manner or separating the components of the reaction.

In an alternative method using a thermostable enzyme, in step (a) the primers, enzyme and nucleotide triphosphates are contacted with the nucleic acid sample. In step (b) the mixture is contacted with the mixture is treated to denature the nucleic acids and then incubated at a temperature at which the primers can hybridize to complementary sequences in the nucleic acid sample. In step (c) the mixture is heated for an effective time and at an effective temperature to promote the activity of the enzyme, and to synthesize, for each different sequence being amplified, an extension product of each primer which is complementary to each nucleic acid strand template, but not so high as to separate each extension product from its complementary strand template.

In step (d) the mixture is heated for an effective time and at an effective temperature to separate the primer extension products from the templates on which they were synthesized to produce single-stranded molecules, but not so high as to denature the enzyme irreversibly. In step (e) the mixture is cooled for an effective time and to an effective temperature to promote hybridization of each primer to each of the single-stranded molecules produced in step (d). Finally, in step (f) the mixture is heated for an effective time and to an effective temperature to promote the activity of the enzyme and to synthesize, for each different sequence being amplified, an extension product of each primer which is complementary to each nucleic acid strand template produced in step (d), but not so high as to separate each extension product from its complementary strand template, where steps (e) and (f) may be carried out simultaneously or sequentially. A more complete description of this process can be found in now abandoned U.S. Ser. No. 899,241, filed Aug. 22, 1986.

A preferred thermostable enzyme which may be employed in the process herein is extracted and purified from Thermus aquaticus and has a molecular weight of about 86,000–90,000 daltons. This enzyme is more fully described in copending U.S. application Ser. No. (Cetus Case 2303) filed concurrently herewith, supra, the disclosure of which is incorporated herein by reference, and in an example below.

The process of the present invention may be conducted continuously. In one preferred embodiment of an automated process wherein a thermostable enzyme is employed, the reaction may be cycled through a denaturing region, a primer annealing region, and a reaction region. In another embodiment, the enzyme used for the synthesis of primer extension products can be immobilized in a column. The other reaction components can be continuously circulated by a pump through the column and a heating coil in series, thus the nucleic acids produced can be repeatedly denatured without inactivating the enzyme.

In one preferred embodiment even where a thermostable enzyme is not employed and the temperature is raised and lowered, one such instrument is the automated machine for handling the amplification reaction of this invention described in now abandoned U.S. Ser. No. 833,368 filed Feb. 25, 1986 entitled "Apparatus And Method For Performing Automated Amplification of Nucleic Acid Sequences And Assays Using Heating And Cooling Steps," the disclosure of which is incorporated herein by reference. Briefly, this instrument utilizes a liquid handling system under computer control to make liquid transfers of enzyme stored at a controlled temperature in a first receptacle into a second receptacle whose temperature is controlled by the computer to conform to a certain incubation profile. The second receptacle stores the nucleic acid sequence(s) to be amplified plus the nucleotide triphosphates and primers. The computer includes a user interface through which a user can enter process parameters which control the characteristics of the various steps in the amplification sequence such as the times and temperatures of incubation, the amount of enzyme to transfer, etc.

A preferred machine which may be employed which is specifically adapted for use with a thermostable enzyme utilizes temperature cycling without a liquid handling system because the enzyme need not be transferred at every cycle. Such a machine is described more completely in copending U.S. application Ser. No. 899,661, filed Aug. 22, 1986, entitled "Apparatus and Method for Performing Automated Amplification of Nucleic Acid Sequences and Assays Using Heating and Cooling Steps," the disclosure of which is incorporated herein by reference. Briefly, this instrument consists of the following systems:

1. A heat-conducting container for holding a given number of tubes, preferably 500 μl tubes, which contain the reaction mixture of nucleotide triphosphates, primers, nucleic acid sequences, and enzyme.

2. A means to heat, cool, and maintain the heat-conducting container above and below room temperature, which means has an input for receiving a control signal for controlling which of the temperatures at or to which the container is heated, cooled or maintained. (This may be Peltier heat pumps available from Materials Electronics Products Corporation in Trenton, N.J. or a water heat exchanger.)

3. A computer means (e.g., a microprocessor controller), coupled to the input of said means, to generate the signals which control automatically the amplification sequence, the temperature levels, and the temperature ramping and timing.

The present invention is demonstrated diagrammatically below where double-stranded DNA containing the desired sequence [S] comprised of complementary strands [S⁺] and [S⁻] is utilized as the nucleic acid. During the first and each subsequent reaction cycle extension of each oligonucleotide primer on the original template will produce one new ssDNA molecule product of indefinite length which terminates with only one of the primers. These products, hereafter referred to as "long products," will accumulate in a linear fashion; that is, the amount present after any number of cycles will be proportional to the number of cycles.

The long products thus produced will act as templates for one or the other of the oligonucleotide primers during subsequent cycles and will produce molecules of the desired sequence [S⁺] or [S⁻] These molecules will also function as templates for one or the other of the oligonucleotide primers, producing further [S⁺] and [S⁻], and thus a chain reaction can be sustained which will result in the accumulation of [S] at an exponential rate relative to the number of cycles.

By-products formed by oligonucleotide hybridizations other than those intended are not self-catalytic (except in rare instances) and thus accumulate at a linear rate.

The specific sequence to be amplified, [S], can be depicted diagrammatically as:

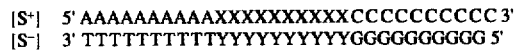

The appropriate oligonucleotide primers would be:
Primer 1: GGGGGGGGGG
Primer 2: AAAAAAAAAA
so that if DNA containing [S]

is separated into single strands and its single strands are hybridized to Primers 1 and 2, the following extension reactions can be catalyzed by DNA polymerase in the presence of the four deoxyribonucleoside triphosphates:

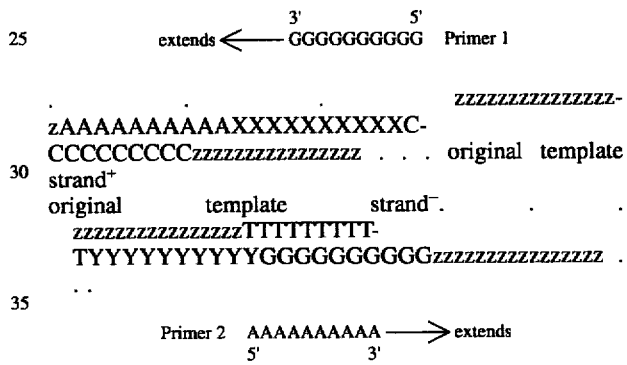

On denaturation of the two duplexes formed, the products are:

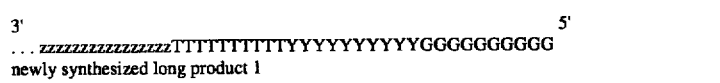
newly synthesized long product 1

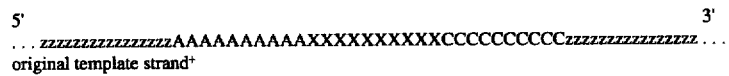
original template strand⁺

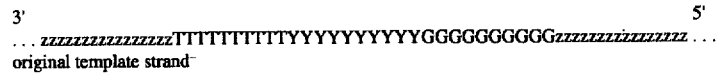
original template strand⁻

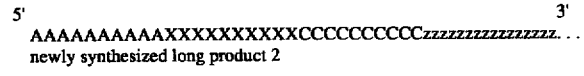
newly synthesized long product 2

If these four strands are allowed to rehybridize with Primers 1 and 2 in the next cycle, the agent for polymerization will catalyze the following reactions:

long product 1

```
              extends ⟵——GGGGGGGGGG 5'  Primer 1

5'.          .          .                    zzzzzzzzzzzzz-
zAAAAAAAAAAXXXXXXXXXXC-
CCCCCCCCCCzzzzzzzzzzzzzz . . . 3'original template
strand⁺

Primer 2   5' AAAAAAAAAA ——⟶ extends

3'.        .        .        zzzzzzzzzzzzzzzzzzzzTTTTTTTTT-
TYYYYYYYYYGGGGGGGGGGGzzzzzzzzzz . . . 5'origi-
nal template strand⁻ extends to here ⟵——GGGGGGGGGG 5'  Primer 1

5'AAAAAAAAAAXXXXXXXXXXC-
    CCCCCCCCCCzzzzzzzzzzzzzzzzz . . . 3'newly synthe-
    sized long product 2
```

If the strands of the above four duplexes are separated, the following strands are found:

```
   5' AAAAAAAAAAXXXXXXXXXXCCCCCCCCCC 3'
            newly synthesized [S⁺]

3'.      .       .    zzzzzzzzzzzzzzzzzzzzTTTTTTTTT-
TYYYYYYYYYGGGGGGGGGGG  5'first cycle synthe-
sized long product 1
3'.      .       .    zzzzzzzzzzzzzzzzzzzzTTTTTTTTT-
TYYYYYYYYYGGGGGGGGGGG  5'newly synthe-
sized long product 1
5'.       .       .              zzzzzzzzzzzzzzzzz-
zAAAAAAAAAAXXXXXXXXXXC-
CCCCCCCCCCzzzzzzzz . . . 3'original template strand⁺
5'AAAAAAAAAAXXXXXXXXXXC-
    CCCCCCCCCCzzzzzzzzzzzzzzzzz . . .3'newly synthe-
    sized long product 2
3'.     .      .        zzzzzzzzzzzzzzzzTTTTTTTTT-
TYYYYYYYYYGGGGGGGGGGGzzzzzzzzzzzzzzzz .
. .5'original template strand⁻
3'TTTTTTTTTTTYYYYYYYYYYYGGGGGGGGGG
    5'newly synthesized [S⁻]
5'AAAAAAAAAAXXXXXXXXXXC-
    CCCCCCCCCCzzzzzzzzzzzzzzzzz . . . 3'first cycle syn-
    thesized long product 2
```

It is seen that each strand which terminates with the oligonucleotide sequence of one primer and the complementary sequence of the other is the specific nucleic acid sequence [S] that is desired to be produced.

The steps of this process can be repeated indefinitely, being limited only by the amount of Primers 1 and 2, agent for polymerization and nucleotides present. The amount of original nucleic acid remains constant in the entire process, because it is not replicated. The amount of the long products increases linearly because they are produced only from the original nucleic acid. The amount of the specific sequence increases exponentially. Thus, the specific sequence will become the predominant species. This is illustrated in the following table, which indicates the relative amounts of the species theoretically present after n cycles, assuming 100% efficiency at each cycle:

| Cycle Number | Number of Double Strands After 0 to n Cycles | | |
|---|---|---|---|
| | Template | Long Products | Specific Sequence [S] |
| 0 | 1 | — | — |
| 1 | 1 | 1 | 0 |
| 2 | 1 | 2 | 1 |
| 3 | 1 | 3 | 4 |
| 5 | 1 | 5 | 26 |
| 10 | 1 | 10 | 1013 |
| 15 | 1 | 15 | 32,752 |
| 20 | 1 | 20 | 1,048,555 |
| n | 1 | n | $(2^n-n-1)$ |

When a single-stranded nucleic acid is utilized as the template, only one long product is formed per cycle.

The desired amount of cycles of this reaction will depend on, e.g., the nature of the sample. Fewer cycles will be required if the sample being analyzed is pure. If the sample is a complex mixture of nucleic acids, more cycles will be required to amplify the signal sufficiently for it to be detected by the method herein. For human genomic DNA preferably 15–30 cycles are carried out to amplify the sequence sufficiently that a clearly detectable signal is produced (i.e., so that background noise does not interfere with detection).

In one embodiment of the invention herein, the amplified sample suspected of containing the sequence variation, whether resulting from cancer, an infectious disease, a genetic disease, or just normal genetic polymorphism, is spotted directly on a series of membranes and each membrane is hybridized with a different labeled sequence-specific oligonucleotide probe. One procedure for spotting the sample on a membrane is described by Kafotos et al., *Nucleic Acids Research*, 7:1541–1552 (1979), the disclosure of which is incorporated herein by reference.

Briefly, the DNA sample affixed to the membrane may be pretreated with a prehybridization solution containing sodium dodecyl sulfate, Ficoll, serum albumin and various salts prior to the probe being added. Then, a labeled oligonucleotide probe which is specific to each sequence to be detected is added to a hybridization solution similar to the prehybridization solution. The hybridization solution is applied to the membrane and the membrane is subjected to hybridization conditions that will depend on the probe type and length, type and concentration of ingredients, etc. Generally, hybridization is carried out at about 25°–75° C., preferably 35° to 65° C., for 0.25–50 hours, preferably less than three hours. The greater the stringency of conditions, the greater the required complementarity for hybridization between the probe and sample. If the background level is high, stringency may be increased accordingly. The stringency can also be incorporated in the wash.

After the hybridization the sample is washed of unhybridized probe using any suitable means such as by washing one or more times with varying concentrations of standard saline phosphate EDTA (SSPE) (180 mM NaCl, 10 mM NaCl, 10 mM $NaHPO_4$ and 1M EDTA, pH 7.4) solutions at 25°–75° C. for about 10 minutes to one hour, depending on the temperature. The label is then detected by using any appropriate detection techniques.

The sequence-specific oligonucleotide employed herein is an oligonucleotide which is generally prepared and selected as described above for preparing and selecting the primers. The sequence-specific oligonucleotide must encompass the region of the sequence which spans the nucleotide variation being detected and must be specific for the nucleotide variation being detected. For example, if it is desired to detect whether a sample contains the mutation for sickle cell anemia, one oligonucleotide will be prepared which contains the nucleotide sequence site characteristic of the normal β-globin gene, and one oligonucleotide will be prepared which contains the nucleotide sequence characteristic of the sickle cell allele. Each oligonucleotide would be hybridized to duplicates of the same sample to determine whether the sample contains the mutation.

The polymorphic areas of HLA class II genes are localized to specific regions of the second exon and are flanked by conserved sequences, so that oligonucleotide primers complementary to opposite strands of the conserved 5' and 3' ends of the second exon can be prepared.

The number of oligonucleotides employed for detection of the polymorphic areas of the HLA class II genes will vary depending on the type of gene, which has regions of base pair variation which may be clustered or spread apart. If the regions are clustered, as in the case with HLA-DQα, then one oligonucleotide is employed for each allele. If the regions are spread apart, as in the case with HLA-DQβ and HLA-DRβ, then more than one probe, each encompassing an allelic variant, will be used for each allele. In the case of HLA-DQβ and HLA-DRβ, three probes are employed for the three regions of the locus where allelic variations may occur. For detection of sequences associated with insulin-dependent diabetes mellitus (IDDM) four probes for the HLA-DRβ second exon are employed.

Haplotypes can be inferred from segregati on analysis in families or, in some cases, by direct analysis of the individual DNA sample. Specific allelic combinations (haplotypes) of sequence-specific oligonucleotide reactivities can be identified in heterozygous cells by using restriction enzyme digestion of the genomic DNA prior to amplification.

For example, if in DQβ one finds three highly variable subregions A, B, and C within a single amplified region, and if there are six different sequences at each region (A1–6, B1–6, C1–6), then an individual could be typed in the DQβ locus by sequence-specific oligonucleotide probe analysis as containing A1, A2; B2, B3; C1, C4, with the possible haplotype combinations of A1, B2, C1; A1, B2, C4; A2, B2, C1; A2, B2, C4; A1, B3, C1; A1, B3, C4; A1, B2, C1; and A1, B2, C4.

If the genomic DNA is digested with a polymorphic restriction enzyme prior to amplification, and if the enzyme cuts both alleles between the primers, there is no reactivity with the sequence-specific probes due to lack of amplification, and the result is uninformative. If the enzyme cuts neither allele, the probe results with digested and undigested genomic DNA are the same and the result is uninformative. If the enzyme cuts only one allele, however, then one can infer both haplotypes by comparing the probe reactivity patterns on digested and undigested DNA.

The haplotypes can be deduced by comparing sequence-specific oligonucleotide reactivities with uncut genomic DNA and genomic DNA cut with one or several enzymes known to be polymorphic and to recognize sites between the primers.

The length of the sequence-specific oligonucleotide will depend on many factors, including the particular target molecule being detected, the source of oligonucleotide, and the nucleotide composition. For purposes herein, the probe typically contains 15–25 nucleotides, although it may contain more or fewer nucleotides. While oligonucleotides which are at least 19-mers in length may enhance specificity and/or sensitivity, probes which are less than 19-mers, e.g., 16-mers, show more sequence-specific discrimination, presumably because a single mismatch is more destabilizing. Because amplification increases specificity so that a longer length is less critical, and hybridization and washing temperatures can be lowered for the same salt concentration, it is preferred to use probes which are less than 19-mers.

Where the sample is first placed on the membrane and then detected with the oligonucleotide, the oligonucleotide must be labeled with a suitable label moiety, which may be detected by spectroscopic, photochemical, biochemical, immunochemical or chemical means. Immunochemical means include antibodies which are capable of forming a complex with the oligonucleotide under suitable conditions, and biochemical means include polypeptides or lectins capable of forming a complex with the oligonucleotide under the appropriate conditions. Examples include fluorescent dyes, electron-dense reagents, enzymes capable of depositing insoluble reaction products or being detected chromogenically, such as alkaline phosphatase, a radioactive label such as $^{32}$p, or biotin. If biotin is employed, a spacer arm may be utilized to attach it to the oligonucleotide.

Alternatively, in one "reverse" dot blot format, at least one of the primers and/or at least one of the four nucleoside triphosphates is labeled with a detectable label, so that the resulting amplified sequence is labeled. These labeled moieties may be present initially in the reaction mixture or added during a later cycle. Then an unlabeled sequence-specific oligonucleotide capable of hybridizing with the amplified nucleic acid sequence, if the variation(s) in sequence (whether normal or mutant) is/are present, is spotted on (affixed to) the membrane under prehybridization conditions as described above. The amplified sample is then added to the pretreated membrane under hybridization conditions as described above. Finally, detection means are used to determine if an amplified sequence in the nucleic acid sample has hybridized to the oligonucleotide affixed to the membrane. Hybridization will occur only if the membrane-bound sequence containing the variation is present in the amplification product, i.e., only if a sequence of the probe is complementary to a region of the amplified sequence.

In another version of the "reverse" dot blot format, the amplification is carried out without employing a label as with the "forward" dot blot format described above, and a labeled sequence-specific oligonucleotide probe capable of hybridizing with the amplified nucleic acid sequence containing the variation, if present, is spotted on (affixed to) the membrane under prehybridization conditions as described above. The amplified sample is then added to the pretreated membrane under hybridization conditions as described above. Then the labeled oligonucleotide or a fragment thereof is released from the membrane in such a way that a detection means can be used to determine if an amplified sequence in the sample hybridized to the labeled oligonucleotide. The release may take place, for example, by adding a restriction enzyme to the membrane which recognizes a restriction site in the probe. This procedure, known as oligomer restriction, is described more fully in EP Patent Publication 164,054 published Dec. 11, 1985, the disclosure of which is incorporated herein by reference.

For purposes of this invention, the genetic diseases which may be detected include specific deletions, insertions and/or substitutions in any base pair mutation or polymorphism in nucleic acids, for example, genomic DNA, from any organism. Examples of diseases in which a base pair variation is known include sickle cell anemia, hemoglobin C disease, α-thalassemia, β-thalassemia, and the like. Other diseases that may be detected include cancerous diseases such as those involving the RAS oncogenes, e.g., the n-RAS oncogene, and infectious diseases.

The process herein may also be used for HLA typing in the areas of tissue transplantation, disease susceptibility, and paternity determination. The HLA class II genes, consisting of the α and β genes from the HLA-DR, HLA-DQ and HLA-DP regions, are highly polymorphic; their genetic complexity at the DNA level is significantly greater than the polymorphism currently defined by serological typing. In addition, the process herein may be employed to detect certain DNA sequences coding for HLA class II β proteins (e.g., DRβ) associated with insulin-dependent diabetes mellitus (IDDM), as described more fully in now abandoned U.S. Ser. No. 899,512, filed Aug. 22, 1986, entitled "Characterization and Detection of Sequences Associated With Insulin-Dependent Diabetes," the disclosure of which is incorporated herein by reference. Briefly, the four DNA sequences associated with IDDM are selected from the group consisting of:

1) 5'-GAGCTGCGTAAGTCTGAG-3', 2) 5'-GAGGAGTTCCTGCGCTTC-3', 3) 5'-CCTGTCGCCGAGTCCTGG-3', and 4) 5'-GACATCCTGGAAGACGAGAGA-3', or the DNA strands that are complementary thereto. Sequence-specific probes may be prepared that will hybridize to one or more of these sequences.

The invention herein also contemplates a kit format which comprises a packaged multicontainer unit having containers for each primer and probe utilized, a container with the agent for polymerization to synthesize the primer extension products, such as enzymes, a container for each of the four nucleotides, and a container with means to detect the label (such as an avidin-enzyme conjugate and enzyme substrate and chromogen if the label is biotin). In addition, the kit may have a container which includes a positive control for the probe containing one or more nucleic acids with the nucleotide variation to be detected and a negative control for the probe which does not contain the nucleic acids with the nucleotide variation to be detected. Moreover, the kit may also have a container with means for separating the strands of any double-stranded nucleic acids contained in the sample such as a helicase or sodium hydroxide.

The following examples illustrate various embodiments of the invention and are not intended to be limiting in any respect. In the examples all parts and percentages are by weight if solid and by volume if liquid, and all temperatures are in degrees Celsius, unless otherwise indicated.

EXAMPLE I

This example illustrates how the process herein can be used to distinguish normal alleles (A) from sickle cell alleles (S) from Hemoglobin C disease alleles (C).

I. Synthesis of the Primers

The following two oligonucleotide primers were prepared by the method described below:

5'-ACACAACTGTGTTCACTAGC-3'     (PC03)

5'-CAACTTCATCCACGTTCACC-3'     (PC04)

These primers, both 20-mers, anneal to opposite strands of the genomic DNA with their 5' ends separated by a distance of 110 base pairs.

A. Automated Synthesis Procedures: The diethylphosphoramidites, synthesized according to Beaucage and Caruthers (*Tetrahedron Letters* (1981) 22:1859–1862)were sequentially condensed to a nucleoside derivatized controlled pore glass support using a Biosearch SAM-1. The procedure included detritylation with trichloroacetic acid in dichloromethane, condensation using benzotriazole as activating proton donor, and capping with acetic anhydride and dimethylaminopyridine in tetrahydrofuran and pyridine. Cycle time was approximately 30 minutes. Yields at each step were essentially quantitative and were determined by collection and spectroscopic examination of the dimethoxytrityl alcohol released during detritylation.

B. Oligodeoxyribonucleotide Deprotection and Purification Procedures: The solid support was removed from the column and exposed to 1 ml concentrated ammonium hydroxide at room temperature for four hours in a closed tube. The support was then removed by filtration and the solution containing the partially protected oligodeoxynucleotide was brought to 55° C. for five hours. Ammonia was removed and the residue was applied to a preparative polyacrylamide gel. Electrophoresis was carried out at 30 volts/cm for 90 minutes after which the band containing the product was identified by UV shadowing of a fluorescent plate. The band was excised and eluted with 1 ml distilled water overnight at 4° C. This solution was applied to an Altech RP18 column and eluted with a 7–13% gradient of acetonitrile in 1% ammonium acetate buffer at pH 6.0. The elution was monitored by UV absorbance at 260 nm and the appropriate fraction collected, quantitated by UV absorbance in a fixed volume and evaporated to dryness at room temperature in a vacuum centrifuge.

C. Characterization of Oligodeoxyribonucleotides: Test aliquots of the purified oligonucleotides were $^{32}$p labeled with polynucleotide kinase and $\gamma$-$^{32}$P-ATP. The labeled compounds were examined by autoradiography of 14–20% polyacryl amide gels after electrophoresis for 45 minutes at 50 volts/cm. This procedure verifies the molecular weight. Base composition was determined by digestion of the oligodeoxyribonucleotide to nucleosides by use of venom diesterase and bacterial alkaline phosphatase and subsequent separation and quantitation of the derived nucleosides using a reverse phase HPLC column and a 10% acetonitrile, 1% ammonium acetate mobile phase.

II. Isolation of Human Genomic DNA from Cell Line

High molecular weight genomic DNA was isolated from the lymphoid cell line GM2064 using essentially the method of Maniatis et al., *Molecular Cloning* (1982), 280–281. GM2064 (Human Mutant Cell Repository, Camden, N.J.) was originally isolated from an individual homozygous for hereditary persistence of fetal hemoglobin (HPFH) and contains no β- or δ-globin gene sequences. This cell line was maintained in RPMI-1640 with 10% fetal calf serum.

III. Isolation of Human Genomic DNA from Clinical Samples

Five clinical blood samples designated AA (from a known normal individual), AS (from a known sickle cell carrier), SS (from a known sickle cell individual), SC (from a known sickle cell/hemoglobin C diseased individual), and AC (from a known hemoglobin C disease carrier) were obtained from Dr. Bertram Lubin of Children's Hospital in Oakland, Calif. One clinical DNA sample designated CC (from a known hemoglobin C diseased individual) was obtained from Dr. Stephen Embury of San Francisco General Hospital in San Francisco, Calif.

Genomic DNA from the first five of these samples was prepared from the buffy coat fraction, which is composed primarily of peripheral blood lymphocytes, as described by Saiki et al., *Biotechnology*, 3:1008–1012 (1985).

IV. Amplification Reaction

One microgram of DNA from each of the seven DNA samples (10 µl of 100 µg/ml DNA) was amplified in an initial 100 µl reaction volume containing 10 µl of a solution containing 100 mM Tris.HCl buffer (pH 7.5), 500 mM NaCl, and 100 mM MgCl$_2$, 10 µl of 10 µM of primer PC03, 10 µl of 10 µM of primer PC04, 15 µl of 40 mM dNTP (contains 10 mM each of dATP, dCTP, dGTP and TTP), and 45 µl of water.

Each reaction mixture was held in a heat block set at 95° C. for 10 minutes to denature the DNA. Then each DNA sample underwent 25 cycles of amplification where each cycle was composed of four steps:

(1) spin briefly (10–20 seconds) in microcentrifuge to pellet condensation and transfer the denatured material immediately to a heat block set at 30° C. for two minutes to allow primers and genomic DNA to anneal, (2) add 2 µl of a solution prepared by mixing 39 µl of the Klenow fragment of *E. coli* DNA Polymerase I (New England Biolabs, 5 units/µl), 39 µl of a salt mixture of 100 mM Tris buffer (pH 7.5), 500 mM NaCl and 100 mM MgCl$_2$, and 312 µl of water, (3) allowing the reaction to proceed for two minutes at 30° C., and (4) transferring the samples to the 95° C. heat block for two minutes to denature the newly synthesized DNA, except this reaction was not carried out at the last cycle.

The final reaction volume was 150 µl, and the reaction mixture was stored at −20° C.

V. Synthesis and Phosphorylation of Oligodeoxyribonucleotide Probes

Three labeled DNA probes, designated RS17, RS18 and RS21, of the following sequences were prepared as follows:

| | |
|---|---|
| 5'-*CTCCTAAGGAGAAGTCTGC-3' | (RS17) |
| 5'-*CTCCTGAGGAGAAGTCTGC-3' | (RS18) |
| 5'-*CTCCTGTGGAGAAGTCTGC-3' | (RS21) | where * indicates the label. These probes are 19 bases long and span the fifth through eleventh codons of the gene. RS18 is complementary to the normal β-globin allele (β$^A$), RS21 to the sickle cell anemia allele (β$^S$), and RS17 to the hemoglobin C disease allele (β$^C$). RS17 and RS21 differ from RS18 by a single base. The schematic diagram of primers and probes is given below:

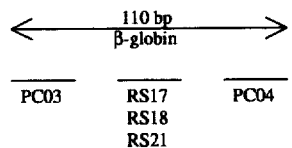

These three probes were synthesized according to the procedures described in Section I. The probes were labeled by contacting 10 pmole thereof with 4 units of T4 polynucleotide kinase (New England Biolabs) and about 40 pmole γ-$^{32}$P-ATP (New England Nuclear, about 7000 Ci/mmole) in a 40 µl reaction volume containing 70 mM Tris buffer (pH 7.6), 10 mM MgCl$_2$, 1.5 mM spermine, 100 mM dithiothreitol and water for 60 minutes at 37° C. The total volume was then adjusted to 100 µl with 25 mM EDTA and purified according to the procedure of Maniatis et al., *Molecular Cloning* (1982), 466–457 over a 1 ml Bio Gel P-4 (BioRad) spin dialysis column equilibrated with Tris-EDTA (TE) buffer (10 mM Tris buffer, 0.1 mM EDTA, pH 8.0). TCA precipitation of the reaction product indicated that for RS17 the specific activity was 5.2 µCi/pmole and the final concentration was 0.118 pmole/µl. For RS18 the specific activity was 4.6 µCi/pmole and the final concentration was 0.114 pmole/µl. For RS21 the specific activity was 3.8 µCi/pmole and the final concentration was 0.112 pmole/µl.

VI. Dot Blot Hybridizations

Five microliters of each of the 150 µl amplified samples from Section III was diluted with 195 µl 0.4N NaOH, 25 mM EDTA and spotted onto three replicate Genatran 45 (Plasco) nylon filters by first wetting the filter with water, placing it in a Bio-Dot (BioRad) apparatus for preparing dot blots which holds the filter in place, applying the samples, and rinsing each well with 0.4 ml of 20×SSPE (3.6M NaCl, 200 mM NaH$_2$PO$_4$, 20 mM EDTA), as disclosed by Reed and Mann, *Nucleic Acids Research*, 13, 7202–7221 (1985). The filters were then removed, rinsed in 20×SSPE, and baked for 30 minutes at 80° C. in a vacuum oven.

After baking, each filter was then contacted with 6 ml of a hybridization solution consisting of 5×SSPE, 5×Denhardt's solution (1×=0.02% polyvinylpyrrolidone, 0.02% Ficoll, 0.02% bovine serum albumin, 0.2 mM Tris.HCl, 0.2 mM EDTA, pH 8.0) and 0.5% SDS and incubated for 60 minutes at 55° C. Then 5 µl each of probes RS17, RS18 and RS21 was added to the hybridization solution and the filter was incubated for 60 minutes at 55° C.

Finally, each hybridized filter was washed twice with 100 ml 2×SSPE and 0.1% SDS for 10 minutes at room temperature. As a third wash for RS17, 250 ml of 5×SSPE and 0.1% SDS was added and the filter heated for five minutes at 55° C. For RS18 and 21, the filters were treated with 250 ml of 4×SSPE, 0.1% SDS for five minutes at 55° C. There was a faint background with RS18 and RS21 because 4×SSPE at 55° C. was not sufficiently stringent. The washing with the RS18 and RS21 probes was repeated in 250 ml of 5×SSPE, 0.1% SDS for three minutes at 55° C. There was no change in the background. The wash was repeated with 5×SSPE at 60° C. for one minute and an additional wash of the same stringency was done for three minutes. This resulted in virtually no background. The genotypes were readily apparent after 90 minutes of autoradiography.

VII. Discussion of Autoradiogram

The autoradiogram of the dot blot of the seven amplified genomic DNA samples hybridized with allele-specific β-globin probes RS18, RS21 and RS17 was analyzed after 12 hours. The negative control GM2064 was included. The results clearly indicate that each allele-specific probe annealed only to the DNA samples which had at least one copy of the β-globin allele to which it was perfectly matched. For example, the $\beta^A$-specific probe, RS18, hybridized only to samples AA ($\beta^A\beta^A$), AS ($\beta^A\beta^S$), and AC ($\beta^A\beta^C$).

EXAMPLE II

To determine the minimum levels of detection by dot blot, eight serial dilutions containing 128, 64, 32, 16, 8, 4, 2 and 1 ng of normal genomic DNA were made from sample AA and subjected to 25 cycles of amplification as described in Example I.

As controls, the amplified samples of AA and SS from Example I were similarly diluted as well.

A total of 75 μl (one-half) of each sample was mixed with 125 μl of 0.65N NaOH and 25 mM EDTA and the mixture was applied to a nylon filter. Then the filter was rinsed in 20×SSPE and baked for 30 minutes at 80° C.

The filter was then probed as described in Example I with RS18 (the $\beta^A$ probe) to determine the detection threshold. The prehybridization solution was 8 ml of 5×SSPE, 5×Denhardt's solution, 0.5% SDS for 40 minutes at 55° C. and the hybridization solution was the same plus 10 μl of RS18 for 80 minutes at 55° C. The filters were then washed with 2×SSPE, 0.1% SDS for 10 minutes at room temperature twice and then with 5×SSPE, 0.1% SDS for three minutes at 60° C.

The autoradiogram obtained after hybridization with RS18 after 17 hours of exposure revealed positive signals in all samples containing the AA DNA. The SS sample was visible after 17 hours but the intensity of the 64 ng SS was equivalent to the intensity of 1 ng AA, which is a signal-to-noise ratio of 64:1. The intensity of the signal present in the 0.5 ng spot suggested that amplification of samples containing significantly less than 1 ng is possible. (One nanogram is the amount of genomic DNA present in 150 diploid cells.)

EXAMPLE III

A. Amplification and Detection of HLA-DQα Sequences

I. Preparation of Primers

Oligonucleotides designated GH26 and GH27 complementary to opposite strands of the conserved 5' and 3' ends of the DQα second exon were used as primers to amplify a 240 base pair fragment. The primers, having the following sequences, were prepared as described in Example I.

| | |
|---|---|
| 5'-GTGCTGCAGGTGTAAACTTGTACCAG-3' | (GH26) |
| 5'-CACGGATCCGGTAGCAGCGGTAGAGTTG-3' | (GH27) |

II. Preparation of Probes

Based on the analysis of HLA-DQα sequences from diverse sources, which were grouped into allelic variants, the following probes from variable regions of the DQα second exon encompassing each variant were synthesized and labeled as described in Example I. The two variable regions of the HLA-DQα second exon (called "exon I"), segments A and B, are shown in Table I. The entire scheme of primers (designated by PCR→), probes and HLA-DQα sequence is shown in Table II, and the amino acid abbreviations used therein are shown in Table III.

TABLE I

```
HLA DQα (segment A):
         35                          40
      Gly Asp Glu Glu Phe Tyr Val Asp Leu Glu Arg Lys Glu
      GGAGATGAGGAGTTCTACGTGGACCTGGAGAGGAAGGAG    DR1,2,w6
      ——————— C ———————————————— A ———————      DR5,8
      ——— C ——————— T ————————————————————      DR4,7,9
      ——————— C ——————————————— G ———————       DR3
DXA:  ——— C ——————— T —————— C ——— A —

HLA DQα (segment B):
         45             50             55             60
      Ala Trp Arg Trp Pro Glu Phe Ser Lys Phe Gly Gly Phe Asp Pro Gln Gly
      GCCTGGCGGTGGCCTGAGTTCAGCAAATTTGGAGGTTTTGACCCGCAGGGT    DR1,2,5,w6,8
      —T——    A —T——— CT ——— C — G ——— A —A- A ———      ATT-  DR4,9
      —T——    AA —T——— CT ——— CA- G-C- A    -A ———      ATT-  DR7
      —T——    T —T-T ——— TTC ——— AC ———  A    -A ———    ATT-  DR3
DXA:  -T——    A —T——— AT — T————————— AT- A ———          A —
```

TABLE II

Alignment of HLA-DQα Protein Sequences

```
Exon-1:                 20                      40                      60                      80
DCAC: DHVASCGVNLYQFYGPSGQYTHEFDGDEEFYVDLERKETAWRWPEFSKFGGFDPQGALRNMAVAKHNLNIMIKRYNSTAATN
DQAH: ———————————————————————————————Q——————————————————————————————————————————————————— (DR1)
PGF1: ———————————————————————————————Q——————————————————————————————————————————————————— (DR2)
CMCC6:———————————————————————————————Q——————————————————————————————————————————————————— (DR2)
DCAS2:———————————————————————————————Q——————————————————————————————————————————————————— (DR6)
FPF1: ————————————F——————————————————Q———————K—————————————————————————————————————————————(DR6)
TAB2: ————————————F——————————————————Q———————K—————————————————————————————————————————————(DR5)
DCAS1:————————————S———————————————————————————————V—QL—L—RR—RR————F——T—I———L————V————S———— (DR8)
MMCC4:————————————S———————————————————————————————V—QL—L—RR—RR————F——T—I———L————V————S———— (DR4)
DCAS3:————————————S———————————————————————————————V—QL—L—RR—RR————F——T—I———L————V————S———— (DR4)
DSAS: ————————————F———————————————————————————————V—KL—L—HRL—R————F——T—I———L————L————S———— (DR9)
DCAP5:————————————S————————————————————G——————————V—CL—L—VLRQ—R———F——T—I———L————SL———S———— (DR7)
CMCC3:————————————S————————————————————G——————————V—CL—L—VLRQ—R———F——T—I———L————SL———S———— (DR3)
         PCR  ────>                                [  A  ][   B   ]                    <──── PCR
```

TABLE III

Amino Acid Abbreviation Codes

| Alaine | Ala | A |
|---|---|---|
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The probes are as follows, where * is the label.

| | |
|---|---|
| 5'-*TGTTTGCCTGTTCTCAGAC-3' | (GH66) |
| 5'-*TTCCGCAGATTTAGAAGAT-3' | (GH67) |
| 5'-*TTCCACAGACTTAGATTTG-3' | (GH68) |
| 5'-*CTCAGGCCACCGCCAGGCA-3' | (GH75) |

The GH75 probe was derived from the DRw6 sequence, which is described by Auffray et al., *Nature*, 308:327 (1984). The GH67 probe was derived from the DR4 sequence, which is described by Auffray et al., *PNAS*, 79:6337 (1982). The GH68 probe was derived from the DR7 sequence which is described by Chang et al., *Nature*, 305:813 (1983). The GH66 probe was derived from the DR3 sequence, which is described by Schenning et al., *EMBO J.*, 3:447 (1984). A control oligonucleotide was derived from a conserved segment of all of these alleles.

III. Origin and Preparation of Genomic DNA

Eleven DNA samples described below were prepared for subsequent amplification as described in Example I.

| | |
|---|---|
| LG2 | cell line (genotype DR1) from Drs. John Bell and Dan Denny of Stanford University, Stanford, California |
| PGF | cell line (genotype DR2) from Drs. John Bell and Dan Denny |
| AVL | cell line (genotype DR3) from Drs. John Bell and Dan Denny |
| DKB | cell line (genotype DR4) from Drs. John Bell and Dan Denny |
| JGL | cell line (genotype DR5) from Dr. Gerry Nepom of Virginia Mason Hospital, Seattle, Washington |
| APD | cell line (genotype DR6) from Drs. John Bell and Dan Denny |
| LBF | cell line (genotype DR7) from Drs. John Bell and Dan Denny |
| TAB | cell line (genotype DR8) from Dr. Gerry Nepom |
| KOZ | cell line (genotype DR9) from Dr. Gerry Nepom |
| | Sample GM2741A (genotype DR1,3) available from the Human Genetic Mutant Cell Repository, Camden, N.J. |
| | Sample GM2676 (genotype DR4,3) available from the Human Genetic Mutant Cell Repository |

IV. Amplification Reaction

Each genomic DNA sample was amplified as described in Example I using GH26 and GH27 as primers for 28 cycles, except that the polymerization step 3 was carried out at 37° C. in the presence of 10% by weight dimethylsulfoxide (DMSO), and except that the amplification reaction took place in the aluminum heating block of the automated liquid handling instrument described in now abandoned U.S. application Ser. No. 833,368 filed Feb. 25, 1986, supra, the disclosure of which is incorporated herein by reference, using the following program:

1) 2.5 min., 37° C. to 98° C. ramp (denature);

2) 3.0 min., 98° C. to 37° C. ramp (anneal);

3) add 1 unit Klenow fragment; and 4) 2.0 min., 37° C. maintain (extend).

V. Dot Blot Hybridization

For each DNA sample, four duplicate nylon filters were spotted with 5 μl of the 150 μl amplified genomic DNA and one of probes GH66, 67, 68 or 75 was applied thereto as described in Example I except that DNA samples were neutralized before application to a Magna Nylon 66 (MSI) filter membrane, using a prehybridization solution of 6×SSPE, 10×Denhardt's solution and 0.5% SDS for one hour at 50° C. and the same solution overnight at 50° C. The filters were washed with 0.1×SSPE, 0.1% SDS for 10–15 minutes at 37° C. The filters were treated as described in Example I to obtain an autoradiogram.

VI. Discussion of Autoradiogram

The autoradiogram of the dot blot shows that the four HLA-DQα allele-specific probes, GH66, GH67, GH68, and GH75 complementary to four HLA-DQα allelic variants, may be used to define nucleotide sequence polymorphisms on amplified DNA from both homozygous and heterozygous individuals. The pattern of reactivity of the probe GH75 corresponds to the serologically defined type DQw1.

B. Amplification and Detection of HLA-DQβ Sequences

I. Preparation of Primers

Oligonucleotides designated GH28 and GH29 complementary to opposite strands of the conserved 5' and 3' ends of the DQ-β second exon were used as primers. The primers, having the following sequences, were prepared as described in Example I.

| | |
|---|---|
| 5'-CTCGGATCCGCATGTGCTACTTCACCAACG-3' | (GH28) |
| 5'-GAGCTGCAGGTAGTTGTGTCTGCACAC-3' | (GH29) |

II. Preparation of Probes

Based on the analysis of HLA-DQβ sequences from diverse sources, which were grouped into allelic variants, the following probes from two variable regions of the DQβ second exon encompassing each variant were synthesized and labeled as described in Example I. The two regions, segments A (GH69–71) and B (GH60–62), as well as a third variable region, are shown in Table IV, The entire scheme of primers, probes and HLA-DQβ sequence is shown in Table V, where the amino acid abbreviations are shown in Table III above.

TABLE IV

HLA-DQβ (segment A):

```
        20                  25                  30
        Gly Thr Glu Arg Val Arg Gly Val Thr Arg His Ile Tyr
        GGG ACG GAG CGC GTG CGG GGT GTG ACC AGA CAC ATC TAT    DR1
        ———————————————TCT———————————T——————————             DR2,4
        ———————————————TCT———A————————————————————           DR6
        ————C—————————————————————————T——————————            DR8
        ————C———T—————————————————————T——————————            DR4"
        ————A———————————TCT———————G———AG—————————             DR3,7
DXB:    ————A———————————C———————G———T————————————
```

HLA-DQβ (segment B):

```
             45                  50                  55                  60
        Val Gly Val Tyr Arg Ala Val Thr Pro Gln Gly Arg Pro Val Ala Glu Tyr Trp Asn
        GTG GGG GTG TAC CGG GCA GTG ACG CCG CAG GGG CGG CCT GTT GCC GAG TAC TGG AAC    DR1
        ——————————————C—G———————————————————————————A————————————————————           DR2
        ————————————————G—————————————————————————————————————————————————           DR6
        ——————————T———G—————————T———C———CC————————————————————                        DR4
        ———A————————G—————————T———C———AC————————————————                              DR4'
        ——————————T———G—————————T———T—AC———————————————————T                          DR8
        —————————A—T———G—————————T—T———T———CC—————————————                            DR3,7
DXB:    —T————A—T—A———G————CGA—T—————AGCA—C—AG—C——————
```

HLA-DQβ (segment C):

```
             65                  70                  75
        Glu Val Leu Glu Gly Ala Arg Ala Ser Val Asp Arg Val
        GAA GTC CTG GAG GGG GCC CGG GCG TCG GTG GAC AGG GTG    DR1
        ——————————————————A—————————GA—T—————C———             DR2
        ————————————A—A—————————GA—T—————C———                 DR4,6
        —CA—————————A—A————————————————CC———                  DR8
        —CA————————A—AAA—————G—————————————                   DR3,7
        —CT—T———CA—AG———CG—————————A————
```

TABLE V

Alignment of HLA-DQβ Protein Sequence

```
                    20                  40                  60                  80
Exon-I:
DCBPG: DFVYQFKGMCYFTNGTERVRLVTRYIYNREEYARFDSDVGVYRAVTPLGPPAAEYWNSQKEVLERTRAELDTVCRHNYQLELRTTLQRR (DR4,3)
JoanP: ————————————————————————————————————————E————D————————————————————————————————————————————— (DR4)
MMCC4: ————————————————————Y———————————————————————————————————————————————————————————————————— (DR4')
NIN:   —————————————————————————————————————————————————RLD——————————DI——ED——SV—————————————————— (DR8)
ARC:   ————————————————————G————————————————————E—————————RLD——————————DI——ED——SV—————————————————— (DR8,7)
DO96:  ————————————————————G————————————————————E—————————RLD——————————DI——ED——SV—————————————————— (DR4")
DQBS3: ——————F——————————L—G———————————————————————————————————————————————————————————————————————— 
DCBP1: ———————————————————————S—S————VV—————————EF————L——L————————————DI———K——AV—R—————————————————— (DR3,6)
DO96:  ———————————————————————S—S————IV—————————EF————L——L————————————DI———K——AV—R—————————————————— (DR7,8)
CMCC3: ———————————————————————S—S————IV—————————EF————L——L————————————DI———K——AV—R—————————————————— (DR3)
DCBS1: ———————————————————————S—S————V——————————EF————L——L————————————DI———K——AV—R—————————————————— (DR3)
DQBC:  ——————————L——————————G—H——————V——————————————Q—R—V————————————————GA———SV—R———————EVAY—GI——— (DR1)
DCBP2: ——————————L——————————G—H——————V——————————————Q—R—V————————————————GA———SV—R———————EVAY—GI——— (DR1,6)
TAB:   ——————————————————————Y————————DV—————————————Q—R—D—————————LDI————————————G—————————————————— (DR8)
DQBH:  ——————F——————————————————————————————————————Q—R—D————————————————————————G———————EVAF—GI——— (DR2)
PGF:   ————————————————————————————————————————————————Q—R—D————————————————————————G——————————————— (DR2)
CMCC6: ——————————————————————H————————————————————————Q—R—V————————————————————————————————EVGY—GI——— (DR6)
DXB:   ——L V———————————————G—A——————G———————————————EFQ———E———RSI——D——NY—DF——QE——AV—K———EA—————————Q

PCR————>          A          B                   C        <————PCR
```

The probes are as follows, where * is the label and ** indicates the best probes.

| | |
|---|---|
| 5´-*CGGCAGGCGGCCCCAGCGG-3´ | (GH60)** |
| 5´-*CGGCAGGCAGCCCCAGCAG-3´ | (GH61)** |
| 5´-*CAACAGGCCGCCCCTGCGG-3´ | (GH62) |
| 5´-*GATGTGTCTGGTCACACCCCG-3´ | (GH69)** |
| 5´-*GATGCTTCTGCTCACAAGACG-3´ | (GH70) |
| 5´-*GATGTATCTGGTCACAAGACG-3´ | (GH71) |

II. Amplification and Dot Blot Hybridization

Using the method generally described in Example IIIA, the probes were found to have reasonable specificity for the portions of the allele being detected in genomic DNA samples.

C. Amplification and Detection of HLA-DRβ Sequences

I. Preparation of Primers

Oligonucleotides designated GH46 and GH50 complementary to opposite strands of the conserved 5´ and 3´ ends of the DRβ second exon were used as primers. The primers, having the following sequences, were prepared as described in Example I.

| | |
|---|---|
| 5´-CCGGATCCTTCGTGTCCCCACAGCACG-3´ | (GH46) |
| 5´-CTCCCCAACCCCGTAGTTGTGTCTGCA-3´ | (GH50) |

II. Preparation of Probes

Based on the analysis of HLA-DRβ sequences from diverse sources, which were grouped into allelic variants, the following probes from two variable regions of the DRβ second exon encompassing each variant were synthesized and labeled as described in Example I. The two regions, segments A (GH56–59) and B (GH51), are shown in Table VI.

The probes are as follows, where * is the label.

| | |
|---|---|
| 5´-*CTGATCAGGTTCCACACTCG-3´ | (GH51) |
| 5´-*CAGACGTAGAGTACTCC-3´ | (GH56) |
| 5´-*CAGACTTACGCAGCTCC-3´ | (GH57) |
| 5´-*CAGACTTAAGCAGCTCC-3´ | (GH58) |
| 5´-*CATGTTTAACCTGCTCC-3´ | (GH59) |

III. Amplification and Dot Blot Hybridization

Using the method generally described in Example IIIA, the probes were found to have reasonable specificity for the portions of the allele being detected in genomic DNA samples.

IV. Analysis of HLA-DRβ Sequences Associated With IDDM

Several HLA class II beta genes were isolated from clinical blood samples of diverse HLA-typed IDDM individuals (from University of Pittsburgh clinic and from cell lines from IDDM patients available from the Human Genetic Mutant Cell Repository, Camden, N.J.) and non-diabetic controls (homozygous typing cells) using cloning methods. In one such method, which is a standard method, human genomic DNA was isolated from the patient samples using essentially the method of Maniatis et al., *Molecular Cloning* (1982), 280–281 or prepared from the buffy coat fraction, which is composed primarily of peripheral blood lymphocytes, as described by Saiki et al., *Biotechnology*, 3:1008–1012 (1985). This DNA was then cloned as full genomic libraries into bacteriphage vectors, as described in Maniatis, supra, pp. 269–294. Individual clones for the HLA-DRβ genes were selected by hybridization to radioactive cDNA probes (Maniatis, pp. 309–328) and characterized by restriction mapping. See U.S. Pat. No. 4,582,788 issued Apr. 15, 1986. Individual clones from IDDM patients were assigned to DR-typed haplotypes by comparing the clone restriction map with the RFLP segregation pattern within the patient's family. Finally, small fragments of these clones representing the variable second exon were sub-cloned (Maniatis, pp. 390–402) into the M13mp10 cloning vector, which is publicly available from Boehringer-Mannheim.

In an alternative procedure for cloning the genes, amplification of the relevant portion (the second exon) of the gene was carried out from a total of 1 microgram of each isolated human genomic DNA as described in Example I using primers GH46 and GH50, which have non-homologous sequences to act as linker/primers.

The reaction mixtures were subjected to 28 cycles of amplification and then the mixtures were stored at −20° C. Then the following cloning procedure was used for the amplified products.

The reaction mixture was sub-cloned into M13mp10 by first digesting in 50 μl of a buffer containing 50 mM NaCl, 10 mM Tris.HCl, pH 7.8, 10 mM MgCl$_2$, 20 units PstI and 26 units HindIII at 37° C. for 90 minutes. The reaction was stopped by freezing. The volume was adjusted to 110 μl with a buffer containing Tris.HCl and EDTA and loaded onto a 1 ml BioGel P-4 spin dialysis column. One fraction was collected and ethanol precipitated.

The ethanol pellet was resuspended in 15 μl water and adjusted to 20 μl volume containing 50 mM Tris.HCl, pH 7.8, 10 mM MgCl$_2$, 0.5 mM ATP, 10 mM dithiothreitol, 0.5 μg M13mp10 vector digested with PstI and HindIII and 400 units ligase. This mixture was incubated for three hours at 16° C.

Ten microliters of ligation reaction mixture containing Molt 4 DNA was transformed into *E. coli* strain JM103 competent cells, which are publicly available from BRL in Bethesda, Md. The procedure followed for preparing the transformed strain is described in Messing, J. (1981) *Third Cleveland Symposium on Macromolecules:Recombinant DNA*, ed. A. Walton, Elsevier, Amsterdam, 143–153.

Eighteen of the alleles from these two cloning procedures were sequenced. In some of the sequences determined four areas of specific DNA and protein sequence were found to occur in various combinations and to be associated with IDDM. The DNA sequences seen in the genomes of IDDM patients produced an alteration in one to three amino acid residues of the DRβ protein. These four variable regions of the DRβ second exon are found in sequences obtained from many diabetic sources and are identified in now abandoned U.S. Ser. No. 899,512, filed Aug. 22, 1986. These regions can be used for synthesizing primers and probes used for detecting such sequences. These sequences are, using the one-letter amino acid abbreviations, -FL-, V--S, and I-DE, encoded by, respectively, codons 10–13, codons 36–39, codons 57–60, and codons 67–71, of the second exon of the DRβ gene.

V. Primers and Amplification

Primers GH46 and GH50 described in Example CI may be employed to amplify DNA samples to be tested for IDDM. The amplification procedure of Example I or IIIA may be employed, using also 10 μl DMSO.

VI. Expected Synthesis of Probes

Two of four labeled DNA probes, designated GH54 (V--S, 5'CCTGTCGCCGABTCCTGG) and GH78 (I--DE, 5'GACATCCTGGAAGACGAGAGA), respectively, may be employed. These probes may be synthesized as described for the primers and labeled as described above.

VII. Expected Dot Blot Hybridizations

Using the dot blot method generally described in Example I, under stringent conditions, the probes are expected to have reasonable specificity for the portions of the allele being detected in genomic DNA samples.

D. Amplification and Detection of HLA-DPα and DPβ Sequences

The known DPβ sequences, showing the type of polymorphism already known, are depicted in FIG. 6 of Trowsdale et al., *Immunological Reviews*, No. 85 (1985), p 5–43, the entire disclosure of which is incorporated herein by reference, at page 16. Further polymorphisms may be identified. Primers for the conserved segments and probes to the variable segments of these genes can be designed similarly to what is described above.

The nucleotide sequence of DPα alleles obtained from cDNA clones showing the type of polymorphismal ready known are depicted in FIG. 4 of Trowsdale et al., supra, at page 12.

The detection and amplification of such sequences may be clinically useful in bone-marrow transplantations and in tissue typing.

EXAMPLE IV

Frozen Molt 4 cells (a T cell line homozygous for normal β-globin from Human Genetic Mutant Cell Repository, Camden, N.J. as GM2219C), SC1 cells (a EBV-transformed B cell line homozygous for the sickle cell allele from ATCC, Rockville, Md. as CRL8756) and GM2064 cells (control described above having no β-globin or δ-globin sequence) were thawed and resuspended in phosphate buffered saline, such that 10 μl of cells containing cell numbers varying from 37 to 1200 for each type of cell line was obtained. Each cell line was mixed with 35 μl water and then overlaid with mineral oil. The resulting suspension was heated at 95° C. for 10 minutes. Then a total of 55 μl of the reagents used to amplify the cell lines in Example I, including primers PC03 and PC04, was added.

The amplification procedure of Example I can then be used followed by the dot blot procedure. This direct use of the cells eliminates isolating the genomic DNA from the cell line or clinical sample.

EXAMPLE V

The procedure of Example I was used to amplify the genomic DNA from a known normal individual, a known sickle cell individual, and an individual with no β-globin gene sequences (GM2064), except that the amplification was automated as described in Example IIIA.

Three labeled DNA probes, designated RS31, RS32, and RS33, of the following sequences were prepared as follows:

| | |
|---|---|
| 5'-*TCCTGAGGAGAAGTCTG-3' | (RS31) |
| 5'-*CCTGAGGAGAAGTCT-3' | (RS32) |
| 5'-*CTGAGGAGAAGTC-3' | (RS33) | where * indicates the label. These probes are 17, 15, and 13 bases long, respectively, and are complementary to the normal β-globin allele ($β^A$). The probes were synthesized and labeled as described in Example I.

Probes RS32, RS33, and RS18 were tested for specificity for non-amplified cloned normal and sickle-cell globin sequences using the procedure described in Example I, except that the hybridization temperature was reduced from 55° C. to below 32° C. At hybridization temperatures below 55° C. the RS18 (19-mer) did not show specificity unless the salt concentration was reduced. The two shorter probes showed excellent specificity at the higher salt content.

The probes RS31, RS32, RS33, and RS18 were tested against the amplified genomic DNA. Because of the conditions of temperature and salt concentration, the 19-mer showed no specificity at a hybridization temperature of below 32° C. All of the shorter mers did show specificity. These results clearly demonstrate that the shorter probes can be selective, and that the conditions of selectivity were less extreme than those needed for the 19-mer.

The 17-mer globin probe RS31 worked optimally when hybridized below 32° C. in 6×SSPE (with 10×Denhardt's and 0.1% SDS) and then washed in 0.1×SSPE for 10 minutes at 42° C.

The 15-mer globin probe RS32 worked optimally when hybridized below 32° C. in 6×SSPE (with 10×Denhardt's and 0.1% SDS) and then washed in 0.1×SSPE for 10 minutes at 32° C.

The 13-mer globin probe RS33 worked optimally when hybridized below 32° C. in 6×SSPE (with 10×Denhardt's and 0.1% SDS) and then washed in 0.1×SSPE for 10 minutes at 25° C.

EXAMPLE VI

I. Synthesis of the Primers

Two primers identified below were synthesized by the method described in Example I to amplify a portion of the second exon of the β-globin gene:

| | |
|---|---|
| 5'-ATTTTCCCACCCTTAGGCTG-3' | (RS40) |
| 5'-GCTCACTCAGTGTGGCAAAG-3' | (RS42) |

This primer pair defines a 198 base pair amplification product that includes the sites of three relatively common β-thalassemia mutations—the codon 39 non sense mutation, the codon 41–42 frameshift deletion, and the codon 44 frameshift deletion.

Because the β-globin-gene in the region of codons 39 to 42 is exactly homologous to delta-globin, the primers were designed to be specific for and only amplify β-globin. The RS40 primer spans the first intron-second exon junction where there are six base pair mismatches with δ-globin. RS42 is positioned over codons 84 to 91 and also contains six mismatches with δ-globin. These mismatches are sufficient to prevent hybridization of the primers to the δ-globin gene. After 20 cycles of amplification, the overall efficiency of these primers was approximately 80% and corresponded to a 130,000-fold amplification. As expected, the amplification product contained no detectable δ-globin DNA.

II. Isolation of Human Genomic DNA From Clinical Samples

Five genomic clinical DNA samples of various β-thalassemia genotypes were obtained from Drs. Alan Scott and Haig Kazazian (Johns Hopkins University, Baltimore, Md.). These samples were JH1 (normal/39 non), JH2 (39 non/39 non), JH3 (normal/41 deletion), JH4 (17 non/41 del), and JH5 (39 non/44 deletion).

III. Amplification Reaction

One microgram portions of each DNA sample and of Molt 4 as control were diluted into a 100 µl volume with 50 mM NaCl, 10 mM Tris.HCl (pH 7.6), 10 mM MgCl$_2$, 1 µM primer PC03, 1 µM primer PC04, 10% DMSO (v/v), 1.5 mM dATP, 1.5 mM dCTP, 1.5 mM dGTP, and 1.5 mM dTTP and subjected to 25 cycles of automated amplification as described in Example IIIA, adding 1 unit of Klenow fragment at each cycle.

IV. Oligodeoxyribonucleotide Probes

Four DNA probes, designed XX1, XX2, XX3 and XX4 below, were provided by Drs. Scott and Kazazian at Johns Hopkins University:

| | |
|---|---|
| 5'-*CCTTGGACCTAGAGGTTCT-3' | (xx1) |
| 5'-*CCTTGGACCCAGAGGTTCT-3' | (xx2) |
| 5'-*GGTTCTTTGAGTCCTTTGG-3' | (xx3) |
| 5'-*GGTT----GAGTCCTTTGGGGAT-3' | (xx4) | where * indicates the label later attached. The XX1 and XX2 pair was used to detect the codon 39 non-sense mutation, with XX1 complementary to the normal allele and XX2 complementary to the non sense mutant. The other pair of probes was designed to test for the 41–42 frameshift deletion, with XX3 annealing to the normal allele and XX4 to the deletion mutant. Each of the probes was phosphorylated as described in Example I.

V. Dot Blot Hybridizations

Four replicate dot blots were prepared, each spot containing one-eighteenth of the amplification product (56 ng of genomic DNA). Each filter was individually prehybridized in 8 ml 5×SSPE, 5×Denhardt's solution, 0.5% SDS for 15 minutes at 55° C. One-half pmole of each labeled probe (specific activities ranged from 1.8 to 0.7 µCi/pmole) was added and the hybridization was continued for an additional 60 minutes at the same temperature. The filters were washed twice at room temperature in 2×SSPE, 0.1% SDS, for 5–10 minutes per wash, followed by a high-stringency wash in 5×SSPE, 0.1% SDS for 10 minutes at 60° C. Autoradiograms were developed after overnight and two-hour exposures with a single intensification screen.

VI. Autoradiogram Results

The results were consistent with the listed genotypes of each DNA sample. Each probe annealed only to those genomic sequences with which it was perfectly matched.

EXAMPLE VII

The method herein may also be applied for forensic uses, by amplifying a random polymorphic region, e.g., HLA or mitochondrial DNA, to detect, e.g., nucleic acids in any body samples such as, e.g., hair samples, semen and blood samples, and other samples containing DNA. The nucleic acid may be extracted from the sample by any means, and primers and probes are selected based on identifying characteristics or known characteristics of the nucleic acid being detected.

EXAMPLE VIII

I. Synthesis of the Primers

The primers PC03 and PC04 described in Example I were employed herein.

II. Isolation of Human Genomic DNA from Cell Line

High molecular weight genomic DNA was isolated from a T cell line, Molt 4, homozygous for normal β-globin available from the Human Genetic Mutant Cell Depository, Camden, N.J. as GM2219C using essentially the method of Maniatis et al., *Molecular Cloning* (1982), 280–281.

III. Purification of a Polymerase From Thermus aquaticus

Thermus aquaticus strain YT1, available without restriction from the American Type Culture Collection, 12301 Parklawn Drive, Rockville, Md., as ATCC No. 25,104 was grown in flasks in the following medium:

| | |
|---|---|
| Sodium Citrate | 1 mM |
| Potassium Phosphate, pH 7.9 | 5 mM |
| Ammonium Chloride | 10 mM |
| Magnesium Sulfate | 0.2 mM |
| Calcium Chloride | 0.1 mM |
| Sodium Chloride | 1 g/l |
| Yeast Extract | 1 g/l |
| Tryptone | 1 g/l |
| Glucose | 2 g/l |
| Ferrous Sulfate | 0.01 mM |

(The pH was adjusted to 8.0 prior to autoclaving.)

A 10-liter fermentor was inoculated from a seed flask cultured overnight in the above medium at 70° C. A total of 600 ml from the seed flask was used to inoculate 10 liters of the same medium. The pH was controlled at 8.0 with ammonium hydroxide with the dissolved oxygen at 40%, with the temperature at 70° C., and with the stirring rate at 400 rpm.

After growth of the cells, they were purified using the protocol (with slight modification) of Kaledin et al., supra, through the first five stages and using a different protocol for the sixth stage. All six steps were conducted at 4° C. The rate of fractionation on columns was 0.5 column volumes/hour and the volumes of gradients during elution were 10 column volumes.

Briefly, the above culture of the T. aquaticus cells was harvested by centrifugation after nine hours of cultivation, in late log phase, at a cell density of 1.4 g dry weight/l. Twenty grams of cell was resuspended in 80 ml of a buffer consisting of 50 mM Tris.HCl pH 7.5, 0.1 mM EDTA. Cells were lysed and the lysate was centrifuged for two hours at 35,000 rpm in a Beckman TI 45 rotor at 4° C. The supernatant was collected (fraction A) and the protein fraction precipitating between 45 and 75% saturation of ammonium sulfate was collected, dissolved in a buffer consisting of 0.2M potassium phosphate buffer, pH 6.5, 10 mM 2-mercaptoethanol, and 5% glycerine, and finally dialyzed against the same buffer to yield fraction B.

Fraction B was applied to a 2.2×30-cm column of DEAE-cellulose, equilibrated with the above described buffer. The column was then washed with the same buffer and the fractions containing protein (determined by absorbance at 280 nm) were collected. The combined protein fraction was dialyzed against a second buffer, containing 0.01M potassium phosphate buffer, pH 7.5, 10 mM 2-mercaptoethanol, and 5% glycerine, to yield fraction C.

Fraction C was applied to a 2.6×21 -cm column of hydroxyapatite, equilibrated with a second buffer. The column was then washed and the enzyme was eluted with a linear gradient of 0.01–0.5M potassium phosphate buffer, pH 7.5, containing 10 mM 2-mercaptoethanol and 5% glycerine. Fractions containing DNA polymerase activity (90–180 mM potassium phosphate) were combined, concentrated four-fold using an Amicon stirred cell and YM10 membrane, and dialyzed against the second buffer to yield fraction D.

Fraction D was applied to a 1.6×28-cm column of DEAE-cellulose, equilibrated with the second buffer. The column was washed and the polymerase was eluted with a linear gradient of 0.01–0.5M potassium phosphate in the second buffer. The fractions were assayed for contaminating endonuclease(s) and exonuclease(s) by electrophoretically detecting the change in molecular weight of phage λ DNA or supercoiled plasma DNA after incubation with an excess of DNA polymerase (for endonuclease) and after treatment with a restriction enzyme that cleaves the DNA into several fragments (for exonuclease). Only those DNA polymerase fractions (65–95 mM potassium phosphate) having minimal nuclease contamination were pooled. To the pool was added autoclaved gelatin in an amount of 250 µg/ml, and dialysis was conducted against the second buffer to yield Fraction E.

Fraction E was applied to a 9 ml phosphocellulose column and eluted with a 100 ml gradient (0.01–0.4M KCl gradient in 20 mM potassium phosphate buffer pH 7.5). The fractions were assayed for contaminating endo/exonuclease(s) as described above as well as for polymerase activity (by the method of Kaledin et al.) and then pooled. The pooled fractions were dialyzed against the second buffer, then concentrated by dialysis against 50% glycerine and the second buffer.

The molecular weight of the polymerase was determined by SDS PAGE. Marker proteins (Bio-Rad low molecular weight standards) were phosphorylase B (92,500), bovine serum albumin (66,200), ovalbumin (45,000), carbonic anhydrase (31,000), soybean trypsin inhibitor (21,500), and lysozyme (14,400).

Preliminary data suggest that the polymerase has a molecular weight of about 86,000–90,000 daltons, not 62,000–63,000 daltons reported in the literature (e.g., by Kaledin et al.).

IV. Amplification Reaction

One microgram of the genomic DNA described above was diluted in an initial 100 µl aqueous reaction volume containing 25 mM Tris.HCl buffer (pH 8.0), 50 mM KCl, 10 mM MgCl$_2$, 5 mM dithiothreitol, 200 µg/ml gelatin, 1 µM of primer PC03, 1 µM of primer PC04, 1.5 mM dATP, 1.5 mM dCTP, 1.5 mM dGTP and 1.5 mM TTP. The sample was heated for 10 minutes at 98° C. to denature the genomic DNA, then cooled to room temperature. Four microliters of the polymerase from Thermus aquaticus was added to the reaction mixture and overlaid with a 100 µl mineral oil cap. The sample was then placed in the aluminum heating block of the liquid handling and heating instrument described in now abandoned U.S. application Ser. No. 833,368 filed Feb. 25, 1986, the disclosure of which is incorporated herein by reference.

The DNA sample underwent 20 cycles of amplification in the machine, repeating the following program cycle:

1) heating from 37° C. to 98° C. in heating block over a period of 2.5 minutes; and 2) cooling from 98° C. to 37° C. over a period of three minutes to allow the primers and DNA to anneal.

After the last cycle, the sample was incubated for an additional 10 minutes at 55° C. to complete the final extension reaction.

V. Synthesis and Phosphorylation of Oligodeoxyribonucleotide Probes

A labeled DNA probe, designated RS24, of the following sequence was prepared:

5'-*CCCACAGGGCAGTAACGGCAGACTTCTC-
CTCAGGAGTCAG-3'        (RS24)

where * indicates the label. This probe is 40 bases long, spans the fourth through seventeenth codons of the gene, and is complementary to the normal β-globin allele (β$^A$). The schematic diagram of primers and probes is given below:

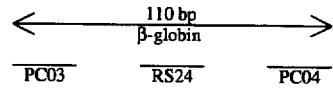

This probe was synthesized according to the procedures described in Section I of Example I. The probe was labeled by contacting 20 pmole thereof with 4 units of T4 polynucleotide kinase (New England Biolabs) and about 40 pmole γ-$^{32}$P-ATP (New England Nuclear, about 7000 Ci/mmole) in a 40 µl reaction volume containing 70 mM Tris buffer (pH 7.6), 10 mM MgCl$_2$, 1.5 mM spermine and 10 mM dithiothreitol for 60 minutes at 37° C. The total volume was then adjusted to 100 µl with 25 mM EDTA and purified according to the procedure of Maniatis et al., *Molecular Cloning* (1982), 466–467 over a 1 ml Bio Gel P-4 (BioRad) spin dialysis column equilibrated with Tris-EDTA (TE) buffer (10 mM Tris buffer, 0.1 mM EDTA, pH 8.0). TCA precipitation of the reaction product indicated that for RS24 the specific activity was 4.3 µCi/pmole and the final concentration was 0.118 pmole/µl.

VI. Dot Blot Hybridizations

Four microliters of the amplified sample from Section I and 5.6 µl of appropriate dilutions of β-globin plasmid DNA calculated to represent amplification efficiencies of 70, 75, 80, 85, 90, 95 and 100% were diluted with 200 μl 10.4N NaOH, 25 mM EDTA and spotted onto a Genatran 45 (Plasco) nylon filter by first wetting the filter with water, placing it in a Bio-Dot (Bio-Rad, Richmond, Calif.) apparatus for preparing dot blots which holds the filters in place, applying the samples, and rinsing each well with 0.1 ml of 20×SSPE (3.6 M NaCl, 200 mM NaH$_2$PO$_4$, 20 mM EDTA), as disclosed by Reed and Mann, *Nucleic Acids Research*, 13, 7202–7221 (1985). The filters were then removed, rinsed in 20×SSPE, and baked for 30 minutes at 80° C. in a vacuum oven.

After baking, each filter was then contacted with 16 ml of a hybridization solution consisting of 3×SSPE, 5×Denhardt's solution (1×=0.02% polyvinylpyrrolidone, 0.02% Ficoll, 0.02% bovine serum albumin,, 0.2 mM Tris, 0.2 mM EDTA, pH 8.0), 0.5% SDS, and 30% formamide, and incubated for two hours at 42° C. Then 2 pmole of probe RS24 was added to the hybridization solution and the filter was incubated for two hours at 42° C.

Finally, each hybridized filter was washed twice with 100 ml of 2×SSPE and 0.1% SDS for 10 minutes at room temperature. Then the filters were treated once with 100 ml of 2×SSPE, 0.1% SDS at 60° C. for 10 minutes.

Each filter was then autoradiographed, with the signal readily apparent after two hours.

VII. Discussion of Autoradiogram

The autoradiogram of the dot blots was analyzed after two hours and compared in intensity to standard serial dilution β-globin reconstructions prepared with HaeIII/MaeI-digested pBR:β$^A$, where β$^A$ is the wild-type allele, as described in Saiki et al., *Science*, supra. Analysis of the reaction product indicated that the overall amplification efficiency was about 95%, corresponding to a 630,000-fold increase in the β-globin target sequence.

EXAMPLE IX

I. Amplification Reaction

Two 1 μg samples of genomic DNA extracted from the Molt 4 cell line as described in Example VIII were each diluted in a 100 μl reaction volume containing 50 mM KCl, 25 mM Tris.HCl buffer pH 8.0, 10 mM MgCl$_2$, 1 μM of primer PC03, 1 μM of primer PC04, 200 μg/ml gelatin, 10% dimethylsulfoxide (by volume), 1.5 mM dATP, 1.5 mM dCTP, 1.5 mM dGTP, and 1.5 mM TTP. After this mixture was heated for 10 minutes at 98° C. to denature the genomic DNA, the samples were cooled to room temperature and 4 μl of the polymerase from Thermus aquaticus described in Example VIII was added to each sample. The samples were overlaid with mineral oil to prevent condensation and evaporative loss.

One of the samples was placed in the heating block of the machine described in Example VIII and subjected to 25 cycles of amplification, repeating the following program cycle:

(1) heating from 37° to 93° C. over a period of 2.5 minutes;

(2) cooling from 93° C. to 37° C. over a period of three minutes to allow the primers and DNA to anneal; and (3) maintaining at 37° C. for two minutes.

After the last cycle the sample was incubated for an additional 10 minutes at 60° C. to complete the final extension reaction.

The second sample was placed in the heat-conducting container of the machine, described in more detail in copending U.S. Ser. No. 899,061, filed Aug. 22, 1986. The heat-conducting container is attached to Peltier heat pumps which adjust the temperature upwards or downwards and a microprocessor controller to control automatically the amplification sequence, the temperature levels, the temperature ramping and the timing of the temperature.

The second sample was subjected to 25 cycles of amplification, repeating the following program cycle:

(1) heating from 37° to 95° C. over a period of three minutes;

(2) maintaining at 95° C. for 0.5 minutes to allow denaturation to occur;

(3) cooling from 95° to 37° C. over a period of one minute; and (4) maintaining at 37° C. for one minute.

II. Analysis

Two tests were done for analysis, a dot blot and an agarose gel analysis.

For the dot blot analysis, a labeled DNA probe, designated RS18, of the following sequence was prepared.

5'-*CTCCTGAGGAGAAGTCTGC-3'    (RS18)

where * indicates the label. This probe is 19 bases long, spans the fourth through seventeenth codons of the gene, and is complementary to the normal β-globin allele (β$^A$). The schematic diagram of primers and probes is given below:

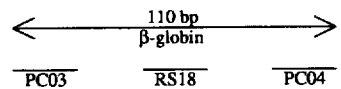

This probe was synthesized according to the procedures described in Section I of Example I. The probe was labeled by contacting 10 pmole thereof with 4 units of T4 polynucleotide kinase (New England Biolabs) and about 40 pmole γ-$^{32}$P-ATP (New England Nuclear, about 7000 Ci/mmole) in a 40 μl reaction volume containing 70 mM Tris.HCl buffer (pH 7.6), 10 mM MgCl$_2$, 1.5 mM spermine and 10 mM dithiothreitol for 60 minutes at 37° C. The total volume was then adjusted to 100 μl with 25 mM EDTA and purified according to the procedure of Maniatis et al., *Molecular Cloning* (1982), 466–467 over a 1 ml Bio Gel P-4 (BioRad) spin dialysis column equilibrated with Tris-EDTA (TE) buffer (10 mM Tris.HCl buffer, 0.1 mM EDTA, pH 8.0). TCA precipitation of the reaction product indicated that for RS18 the specific activity was 4.6 μCi/pmole and the final concentration was 0.114 pmole/μl.

Five microliters of the amplified sample from Section I and of a sample amplified as described above except using the Klenow fragment of *E. coli* DNA Polymerase I instead of the thermostable enzyme were diluted with 195 μl 0.4N NaOH, 25 mM EDTA and spotted onto two replicate Genatran 45 (Plasco) nylon filters by first wetting the filters with water, placing them in a Bio-Dot (Bio-Rad, Richmond, Calif.) apparatus for preparing dot blots which holds the filters in place, applying the samples, and rinsing each well with 0.4 ml of 20×SSPE (3.6M NaCl, 200 mM NaH$_2$PO$_4$, 20 mM EDTA), as disclosed by Reed and Mann, *Nucleic Acids Research*, 13, 7202–7221 (1985). The filters were then removed, rinsed in 20×SSPE, and baked for 30 minutes at 80° C. in a vacuum oven.

After baking, each filter was then contacted with 6 ml of a hybridization solution consisting of 5×SSPE, 5×Denhardt's solution (1×=0.02% polyvinylpyrrolidone, 0.02% Ficoll, 0.02% bovine serum albumin, 0.2 mM Tris, 0.2 mM EDTA, pH 8.0) and 0.5% SDS, and incubated for 60 minutes at 55° C. Then 5 µl of probe RS18 was added to the hybridization solution and the filter was incubated for 60 minutes at 55° C.

Finally, each hybridized filter was washed twice with 100 ml of 2×SSPE and 0.1% SDS for 10 minutes at room temperature. Then the filters were treated twice more with 100 ml of 5×SSPE, 0.1% SDS at 60° C. for 1) one minute and 2) three minutes, respectively.

Each filter was then autoradiographed, with the signal readily apparent after 90 minutes.

In the agarose gel analysis, 5 µl each amplification reaction was loaded onto 4% NuSieve/0.5% agarose gel in 1×TBE buffer (0.089M Tris borate, 0.089M boric acid, and 2 mM EDTA) and electrophoresed for 60 minutes at 100 V. After staining with ethidium bromide, DNA was visualized by UV fluorescence.

The results show that the machines used in Examples VIII and IX herein were equally effective in amplifying the DNA, showing discrete high-intensity 110-base pair bands of similar intensity, corresponding to the desired sequence, as well as a few other discrete bands of much lower intensity. In contrast, the amplification method as described in Example I of now abandoned U.S. Ser. No. 839,331 filed Mar. 13, 1986, supra., which involves reagent transfer after each cycle using the Klenow fragment of *E. coli* Polymerase I, gave a DNA smear resulting from the non-specific amplification of many unrelated DNA sequences.

It is expected that similar improvements in amplification and detection would be achieved in evaluating HLA-DQ, DR and DP regions.

It is also expected that the procedure of Example I may be repeated using a biotinylated probe prepared as described in U.S. Pat. No. 4,582,789 and U.S. Pat. No. 4,617,261, the disclosures of which are incorporated herein by reference.

EXAMPLE X cDNA was made from 1 µg of rabbit reticulocyte mRNA (Bethesda Research Laboratories) in a 100 µl reaction volume containing 150 mM KCl, 50 mM Tris.HCl (pH 8.3), 10 mM MgCl$_2$, 5 mM DTT, 0.5 mM dATP, 0.5 mM dCTP, 0.5 mM dTTP, 0.5 mM dGTP, 0.2 µg oligo(dT)12–18 (Pharmacia), 40 units RNasin (Promega Biotec), and 5 units AMV reverse transcriptase (BRL) and incubated for 30 minutes at 42° C. The reaction was stopped by heating for 10 minutes at 95° C. Two µg RNase A was added to the sample (2 µl of a 2 mg/ml solution in water) and incubated for 10 minutes at 37° C.

Three amplification reactions were done with the Klenow fragment using different pairs of primers. The primer pair PCO3/PCO4 define a 110-bp product, the primer pair RS45/oligo(dT)25–30 define an about 370-bp product, and the primer pair PCO3/oligo(dT)25–30 an about 600-bp product. PCO3, PCO4, and RS45 are complementary to the human β-globin gene and each has two mismatches with the rabbit gene. PCO3 and PCO4 are described in Example I. RS45 has the sequence: 5'-CAAGAAGGTGCTAGGTGCC-3'. Oligo(dT)25–30 was purchased from Pharmacia.

The amplification reactions were performed with 1/20th (5 µl) of the cDNA described above in a 100 µl reaction volume containing 50 mM NaCl, 10 mM Tris.HCl (pH 7.6), 10 mM MgCl$_2$, 200 µg/ml gelatin, 10% DMSO, 1 µM PCO3 or RS45, 1 µM PCO4 or oligo(dT)25–30, 1.5 mM dATP, 1.5 mM dCTP, 1.5 mM dTTP and 1.5 mM dGTP. The samples were heated for five minutes at 98° C., then cooled to room temperature and overlayed with about 100 µl mineral oil.

The samples were subjected to 10 cycles of automated amplification using the machine described in Example VIII and using the following program:

1) heating from 37° C. to 98° C. in heating block over 2.5 minutes (denature);

2) cooling from 98° C. to 37° C. over 3.0 minutes (anneal);

3) adding 1 unit Klenow fragment; and (4) maintaining at 37° C. for 20 minutes (extend).

The final volume of each sample was about 140 µl.

One-twentieth (7 µl) of each sample was analyzed by electrophoresis on a 2% agarose gel. After staining with ethidium bromide, discrete bands were seen in the PCO3/PCO4 and RS45/oligo(dT) samples. The sizes of the bands were consistent with the expected lengths: 110-bp for the former, about 370-bp for the latter. No evidence of amplification of an about 600-bp fragment with the PCO3/oligo(dT) primer pair was observed.

The contents of the gel were Southern blotted onto a Genatran nylon membrane and hybridized with a nick-translated human β-globin probe, pBR328:betaA, described in Saiki et al., *Science*, supra, using standard techniques. The resulting autoradiogram extended the conclusions reached previously—the 110 and about 370-bp fragments were β-globin specific amplification products and no significant amplification of the about 600-bp band was detected.

Three additional samples were amplified with the Thermus aquaticus (Taq) polymerase obtained as described above using the same primer pairs described previously. Five microliter portions of cDNA were amplified in 100 µl reaction volumes containing 50 mM KCl, 25 mM Tris.HCl (pH 8.0), 10 mM MgCl$_2$, 200 µg/ml gelatin, 10% DMSO, 1 µM PCO3 or RS45, 1 µM PCO4 or oligo(dT)25–30, 1.5 mM dATP, 1.5 mM dGTP, 1.5 mM dTTP and 1.5 mM dGTP. The samples were heated for five minutes at 98° C., then cooled to room temperature. One microliter of Taq polymerase (⅛ dilution of lot 2) was added to each and overlayed with about 100 µl mineral oil.

The samples were subjected to 9 cycles of amplification in the Peltier device described in the previous example using the following program:

1) 1 min, 35° to 60° C. ramp;

2) 12 min, 60° to 70° C. ramp (extend);

3) 1 min, 70° to 95° C. ramp (denature);

4) 30 sec, 95° C. soak;

5) 1 min, 95° to 35° C. ramp (anneal); and 6) 30 sec, 35° C. soak.

After the last cycle, the samples were incubated an additional 10 minutes at 60° C. to complete the final (10th cycle) extension. The final volume of each was about 100 µl.

As before, 1/20th (10 µl) of each sample was analyzed on a 2% agarose gel. In this gel, amplification products were present in all three samples: 110-bp for PCO3/PCO4, about 370-bp for RS45/oligo(dT), and about 600-bp for PCO3/oligo(dT). These results were confirmed by Southern transfer and hybridization with the pBR328: betaA probe.

The production of the 600-bp product with Taq polymerase but not with the Klenow fragment is significant, and suggests that Taq polymerase is capable of producing longer DNA than the Klenow fragment.

In summary, the technique herein wherein nucleic acids are amplified in a chain reaction in which primer extension products are produced which can subsequently act as templates, and the amplified samples are analyzed using sequence-specific probes provides several important advantages. It is a simplified procedure because the amplified samples can be spotted on a filter membrane as a dot blot, thereby avoiding the restriction digestion, electrophoresis and gel manipulations otherwise required. It is a more specific procedure because the amplification greatly increases the ratio of specific target sequence to cross-hybridizing sequences.

In addition, the process herein improves sensitivity by $10^3$–$10^4$. An interpretable signal can be obtained with a 1 ng sample after an overnight exposure. Finally, by increasing the amount of sample applied to the filter to 0.1 to 0.5 µg, it is possible that biotinylated oligonucleotide probes may be utilized.

Other modifications of the above described embodiments of the invention that are obvious to those skilled in the area of molecular biology, biochemistry and related disciplines are intended to be within the scope of the following claims.

What is claimed is:

1. A process for detecting the presence of a nucleotide variation in sequence in a nucleic acid contained in a sample, which process comprises:
   (a) treating the sample, together or sequentially, with four different nucleoside triphosphates, an agent for polymerization of the nucleoside triphosphates, and two oligonucleotide primers for said nucleic acid containing said variation under hybridizing conditions, such that a primer hybridizes to said nucleic acid and an extension product of the primer is synthesized which is complementary to said nucleotide variation in sequence, wherein said primers are selected such that the extension product synthesized from one primer, when separated from its complement, can serve as a template for synthesis of the extension product of the other primer;
   (b) treating the sample under denaturing conditions to separate the primer extension products from their templates;
   (c) treating the sample, together or sequentially, with said four nucleoside triphosphates, an agent for polymerization of the nucleoside triphosphates, and oligonucleotide primers such that a primer extension product is synthesized using each of the single strands produced in step (b) as a template, wherein steps (b) and (c) are repeated a sufficient number of times to result in detectable amplification of the nucleic acid containing the sequence variation;
   (d) directly transferring, without gel fractionation, the product of step (c) to a membrane;
   (e) treating the membrane under hybridization conditions with a labeled sequence-specific oligonucleotide probe between about 15 and about 25 nucleotides in length capable of hybridizing with the amplified nucleic acid sequence only if a sequence of the probe is complementary to a region of the amplified sequence; and
   (f) detecting whether the probe has hybridized to an amplified sequence in the nucleic acid sample.

2. The process of claim 1, wherein the nucleic acid in the sample is extracted from the sample prior to step (a), and steps (b) and (c) are repeated at least five times.

3. The process of claim 2, wherein the sample contains human genomic DNA and steps (b) and (c) are repeated 15–30 times.

4. The process of claim 1, wherein said nucleic acid is double-stranded and its strands are separated by denaturing before or during step (a).

5. The process of claim 1, wherein said nucleic acid is single-stranded.

6. The process of claim 4, wherein said nucleic acid is DNA and said primers are oligodeoxyribonucleotides.

7. The process of claim 1, wherein said nucleic acid is messenger RNA and said primers are oligodeoxyribonucleotides.

8. The process of claim 5, wherein said nucleic acid is DNA and said primers are oligodeoxyribonucleotides.

9. The process of claim 5, wherein said nucleic acid is messenger RNA and said primers are oligodeoxyribonucleotides.

10. The process of claim 1, wherein said agent for polymerization is selected from the group consisting of E. coli DNA Polymerase I, Klenow fragment of E. coli DNA Polymerase I, T4 DNA polymerase, a thermostable DNA polymerase enzyme, and a reverse transcriptase.

11. The process of claim 1, wherein the nucleotide variation in sequence is contained within a human nucleic acid selected from the group consisting of a beta-globin gene: an onconene: an HLA-DQα, DQβ, DRβ, DPα and DPβ gene; and mitochondfial DNA.

12. The process of claim 1, wherein the sample is a semen, hair or blood sample, or contains mitochondrial DNA, and the process is used in forensic analysis.

13. The process of claim 1, wherein the nucleotide variation in sequence is contained within nucleic acid of an organism that can cause an infectious disease.

14. The process of claim 1, wherein the sample comprises cells, and the process further comprises, before step (a), the step of heating the sample sufficiently to expose the nucleic acid(s) therein.

15. The process of claim 14, wherein the sample is peripheral blood lymphocytes or amniotic fluid.

16. The process of claim 1, wherein said nucleic acid is human genomic DNA.

17. The process of claim 16 wherein said primers amplify a segment of a class II HLA gene.

18. The process of claim 17, wherein said gene is a DQα allele.

19. The process of claim 17, wherein said gene is a DQβ allele.

20. The process of claim 17, wherein said gene is a DPα allele.

21. The process of claim 17, wherein said gene is a DPβ allele.

22. The process of claim 17, wherein said gene is a DRα allele.

23. The process of claim 17, wherein said gene is a DRβ allele.

24. A kit for detecting the presence of a nucleotide variation in sequence in a nucleic acid contained in a sample, which kit comprises, in packaged form, a multicontainer unit having:
   (a) two oligonucleotide primers for each nucleic acid sequence variation being detected, which primers are selected such that an extension product synthesized from one primer, when separated from its complement, can serve as a template for the synthesis of the extension product of the other primer so as to produce amplified nucleic acid sequences containing the sequence variation;
   (b) an agent for polymerization;
   (c) four different nucleotide triphosphates;

(d) a sequence-specific oligonucleotide probe between about 15 and about 25 nucleotides in length capable of hybridizing with the amplified nucleic acid sequence only if a sequence of the probe is complementary to a region of the amplified sequence; and (e) a membrane to which amplified nucleic acid can bind for subsequent detection by probe hybridization.

25. The kit of claim 24, wherein said primers are oligodeoxyribonucleotides, said nucleotide triphosphates are dATP, dCTP, dGTP and TTP, and the probe is labeled.

26. The kit of claim 24, wherein the agent for polymerization is an enzyme selected from the group consisting of *E. coli* DNA Polymerase I, Klenow fragment of *E. coli* DNA Polymerase I, T4 DNA polymerase, a heat-stable DNA polymerase enzyme, and reverse transcriptase.

27. The kit of claim 24, further comprising a container containing a positive control for the probe which contains one or more nucleic acids with the nucleotide variation to be detected and a negative control for the probe which does not contain the nucleic acids with the nucleotide variation to be detected.

28. The kit of claim 24, wherein the nucleotide variation in sequence is contained within a human nucleic acid selected from the group consisting of a beta-globin gene; an HLA-DQα, DQβ, DRβ, DPα, and DPβ gene, and mitochondrial DNA.

29. A kit for detecting the presence of a nucleotide variation in sequence in a nucleic acid contained in a sample, which kit comprises, in packaged form, a multicontainer unit having:

(a) two oligonucleotide primers for each nucleic acid sequence variation being detected, which primers are selected such that an extension product synthesized from one primer, when separated from its complement, can serve as a template for the synthesis of the extension product of the other primer so as to produce amplified nucleic acid sequences containing the sequence variation; and (b) a sequence-specific oligonucleotide probe about 15 to about 25 nucleotides in length, wherein said probe is capable of hybridizing with the amplified nucleic acid sequence only if a sequence of the probe is complementary to a region of the amplified sequence.

30. The kit of claim 29, wherein said primers and probe are oligodeoxyribonucleotides.

31. The kit of claim 30, which further comprises a DNA polymerase.

32. The kit of claim 31, which further comprises four different nucleoside 5'-triphosphates.

* * * * *